US012075979B2

(12) United States Patent
Gavalis et al.

(10) Patent No.: US 12,075,979 B2
(45) Date of Patent: Sep. 3, 2024

(54) ENDOSCOPE AIR/WATER FLUSH ADAPTOR AND METHOD

(71) Applicant: Boston Scientific Scimed, Inc., Maple Grove, MN (US)

(72) Inventors: Robb M. Gavalis, Westborough, MA (US); Allyn N. Jensrud, Brookline, MA (US); Colby Harris, Weston, MA (US); Larry E. Stanton, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1042 days.

(21) Appl. No.: 16/925,727

(22) Filed: Jul. 10, 2020

(65) Prior Publication Data

US 2021/0007586 A1    Jan. 14, 2021

Related U.S. Application Data

(60) Provisional application No. 62/872,887, filed on Jul. 11, 2019.

(51) Int. Cl.
*A61B 1/00* (2006.01)
*A61B 1/015* (2006.01)
*A61B 1/12* (2006.01)

(52) U.S. Cl.
CPC .............. *A61B 1/015* (2013.01); *A61B 1/125* (2013.01)

(58) Field of Classification Search
CPC ..... A61B 1/015; A61B 1/00068; A61B 1/125; A61B 1/123; A61B 1/12; A61M 2202/02
See application file for complete search history.

(56) References Cited

U.S. PATENT DOCUMENTS

| 3,932,722 | A | 1/1976 | Obata et al. |
| 3,958,566 | A | 5/1976 | Furihata |
| 4,198,958 | A | 4/1980 | Utsugi |
| 4,261,343 | A | 4/1981 | Ouchi et al. |

(Continued)

FOREIGN PATENT DOCUMENTS

| EP | 0055394 A1 | 7/1982 |
| EP | 0069913 A2 | 1/1983 |

(Continued)

OTHER PUBLICATIONS

International Search Report and Written Opinion for the International Patent Application No. PCT/US2020/041549, mailed Sep. 8, 2020, 32 pages.

*Primary Examiner* — Anh T Nguyen
*Assistant Examiner* — Rynae E Boler
(74) *Attorney, Agent, or Firm* — Seager, Tufte & Wickhem, LLP

(57) ABSTRACT

The present disclosure relates generally to the field of medical devices. In particular, the present disclosure relates to devices, systems and methods for air/water and flushing valves. For example, an endoscopic valve of the present disclosure may include a valve stem with contiguous first and second channels and with first and second ports formed within a sidewall of the valve stem. A series of seals may be disposed around an outer surface of the valve stem proximal and distal to the first and second ports. A gating member may be slidably disposed within the proximal channel and a valve insert may be disposed between the proximal and distal channels.

16 Claims, 19 Drawing Sheets

(56) References Cited

U.S. PATENT DOCUMENTS

| | | |
|---|---|---|
| 4,270,525 A | 6/1981 | Furihata |
| 4,361,138 A | 11/1982 | Kinoshita |
| 4,412,531 A | 11/1983 | Chikashige |
| 4,469,090 A | 9/1984 | Konomura |
| 4,537,182 A | 8/1985 | Otani |
| 4,537,209 A | 8/1985 | Sasa |
| 4,561,428 A | 12/1985 | Konomura |
| 4,572,163 A | 2/1986 | Collins et al. |
| 4,656,767 A | 4/1987 | Tarrant |
| 4,667,655 A | 5/1987 | Ogiu et al. |
| 4,694,821 A | 9/1987 | Kondo |
| 4,794,913 A | 1/1989 | Shimonaka et al. |
| 4,800,869 A | 1/1989 | Nakajima |
| 4,969,231 A | 11/1990 | Mader et al. |
| 5,027,791 A | 7/1991 | Takahashi |
| 5,125,910 A | 6/1992 | Freitas |
| 5,293,960 A | 3/1994 | Majerowicz et al. |
| 5,299,561 A | 4/1994 | Yoshimoto |
| 5,343,854 A | 9/1994 | Katsurada |
| 5,391,145 A | 2/1995 | Dorsey, III |
| 5,449,145 A | 9/1995 | Wortrich |
| 5,472,439 A | 12/1995 | Hurd |
| 5,697,888 A | 12/1997 | Kobayashi et al. |
| D390,275 S | 2/1998 | Wolff |
| 5,749,829 A | 5/1998 | Yokoi et al. |
| 5,782,795 A | 7/1998 | Bays |
| 5,795,403 A | 8/1998 | Biermaier |
| 5,795,404 A | 8/1998 | Murphy et al. |
| 5,840,015 A | 11/1998 | Ogino |
| 5,871,441 A | 2/1999 | Ishiguro et al. |
| 5,938,589 A | 8/1999 | Wako |
| 6,119,714 A | 9/2000 | Otzen |
| D436,631 S | 1/2001 | Caloia et al. |
| D438,909 S | 3/2001 | Najmi |
| 6,240,960 B1 | 6/2001 | Fillmore |
| 6,286,179 B1 | 9/2001 | Byrne |
| D453,193 S | 1/2002 | Isaacs et al. |
| 6,346,075 B1 * | 2/2002 | Arai ............... A61B 1/00068 600/159 |
| 6,481,462 B2 | 11/2002 | Fillmore et al. |
| 6,533,720 B1 | 3/2003 | Dhindsa |
| 6,663,598 B1 | 12/2003 | Carillo, Jr. et al. |
| 6,666,818 B2 | 12/2003 | Dhindsa |
| 6,708,948 B2 | 3/2004 | Nösel |
| D490,112 S | 5/2004 | Hadzic et al. |
| 6,786,865 B2 | 9/2004 | Dhindsa |
| 6,823,617 B2 | 11/2004 | Schweikert |
| 6,849,043 B2 | 2/2005 | Kondo |
| 6,863,661 B2 | 3/2005 | Carrillo, Jr. et al. |
| 6,874,517 B2 | 4/2005 | Halstead et al. |
| 6,908,429 B2 | 6/2005 | Heimberger |
| 6,908,449 B2 | 6/2005 | Willis et al. |
| 6,984,204 B2 | 1/2006 | Akiba |
| 7,175,612 B2 | 2/2007 | Felix et al. |
| 7,331,130 B2 | 2/2008 | Schweikert |
| 7,513,071 B2 | 4/2009 | Miyake |
| 7,530,821 B2 | 5/2009 | Miyake |
| 7,901,350 B2 | 3/2011 | Yamazaki |
| 8,235,889 B2 | 8/2012 | Kohno |
| 8,273,014 B2 | 9/2012 | Ushijima et al. |
| 8,382,661 B2 | 2/2013 | Yamane |
| 8,414,478 B2 | 4/2013 | Yamane |
| 8,475,481 B2 | 7/2013 | Himes et al. |
| 8,568,303 B2 | 10/2013 | Yamane |
| 8,579,870 B2 | 11/2013 | Willis et al. |
| 8,740,776 B2 | 6/2014 | Ushijima |
| 8,821,389 B2 | 9/2014 | Yamane |
| 8,870,756 B2 | 10/2014 | Maurice |
| 9,144,374 B2 | 9/2015 | Maurice, Jr. |
| 9,161,680 B2 | 10/2015 | Bellofatto et al. |
| 9,198,683 B2 | 12/2015 | Friedman et al. |
| 9,307,890 B2 | 4/2016 | Ouchi |
| 9,398,842 B2 | 7/2016 | Furuta |
| 9,408,523 B2 | 8/2016 | Grudo et al. |
| 9,414,742 B2 | 8/2016 | Sato |
| 9,492,066 B2 | 11/2016 | Iwasaki |
| 9,560,954 B2 | 2/2017 | Jacobs et al. |
| 9,565,995 B2 | 2/2017 | Nguyen et al. |
| 9,585,545 B2 | 3/2017 | Anderson et al. |
| 9,603,509 B2 | 3/2017 | Ando |
| 9,615,724 B2 | 4/2017 | Murayama |
| 9,622,647 B2 | 4/2017 | Cushner et al. |
| 9,642,512 B2 | 5/2017 | Toyoda |
| 9,775,503 B2 | 10/2017 | Inoue et al. |
| 9,782,525 B2 | 10/2017 | Cheng |
| 9,872,603 B2 | 1/2018 | Sato et al. |
| 9,877,637 B2 | 1/2018 | Nakajima |
| 9,918,615 B2 | 3/2018 | Hamazaki |
| 9,949,623 B2 | 4/2018 | Lang et al. |
| 9,968,242 B2 | 5/2018 | Salman et al. |
| 10,034,603 B2 | 7/2018 | Matsuo et al. |
| 10,098,525 B2 | 10/2018 | Maurice |
| 10,111,578 B2 | 10/2018 | Maurice |
| 10,154,801 B2 | 12/2018 | Friedman et al. |
| 10,188,276 B2 | 1/2019 | Iwasaki |
| 10,238,273 B2 | 3/2019 | Xu et al. |
| 10,314,466 B2 | 6/2019 | Ando |
| D861,161 S | 9/2019 | Schuessler |
| 10,448,814 B2 | 10/2019 | Rebholz et al. |
| 10,456,014 B2 | 10/2019 | Wolcott et al. |
| 10,898,062 B2 | 1/2021 | Wolfe |
| D912,245 S | 3/2021 | Grudo et al. |
| 10,987,453 B2 | 4/2021 | Cheng |
| 2005/0065405 A1 | 3/2005 | Hasegawa |
| 2005/0187524 A1 | 8/2005 | Willis et al. |
| 2006/0041190 A1 | 2/2006 | Sato |
| 2006/0100485 A1 | 5/2006 | Arai et al. |
| 2007/0088323 A1 * | 4/2007 | Campbell ............ A61M 25/10 604/523 |
| 2008/0021280 A1 | 1/2008 | Suzuki |
| 2012/0071843 A1 | 3/2012 | Yamane |
| 2012/0071844 A1 | 3/2012 | Yamane |
| 2012/0085956 A1 | 4/2012 | Morimoto |
| 2012/0088973 A1 | 4/2012 | Morimoto |
| 2012/0088975 A1 * | 4/2012 | Morimoto ......... A61B 1/00068 600/159 |
| 2014/0100424 A1 | 4/2014 | Hoshino |
| 2016/0081538 A1 * | 3/2016 | Rebholz ................ A61B 1/015 600/159 |
| 2016/0130055 A1 | 5/2016 | Labonski |
| 2016/0309987 A1 | 10/2016 | Grudo et al. |
| 2017/0143194 A1 | 5/2017 | Wolfe |
| 2017/0347860 A1 | 12/2017 | Still et al. |
| 2018/0361034 A1 | 12/2018 | Tobien |
| 2019/0035441 A1 | 1/2019 | Bedeschi et al. |
| 2019/0125167 A1 | 5/2019 | Taniguchi |
| 2019/0350444 A1 | 11/2019 | Saiga |
| 2019/0350446 A1 | 11/2019 | Saiga |
| 2020/0016637 A1 | 1/2020 | Still et al. |
| 2020/0375434 A1 * | 12/2020 | Scutti ................ A61B 1/00137 |
| 2020/0386330 A1 * | 12/2020 | Stanton ............... F16K 11/0712 |
| 2021/0145261 A1 | 5/2021 | Still et al. |
| 2021/0177242 A1 | 6/2021 | Remus |
| 2021/0204797 A1 | 7/2021 | Hernandez et al. |
| 2021/0378486 A1 | 12/2021 | McCabe |
| 2021/0378487 A1 | 12/2021 | Lagow et al. |

FOREIGN PATENT DOCUMENTS

| | | |
|---|---|---|
| EP | 0106310 B1 | 1/1987 |
| EP | 0069913 B1 | 3/1987 |
| EP | 0075188 B1 | 11/1987 |
| JP | H08196505 A | 8/1996 |
| JP | H08243080 A | 9/1996 |
| JP | 3015277 B2 | 3/2000 |
| JP | 3375415 B2 | 2/2003 |
| JP | 3431365 B2 | 7/2003 |
| JP | 3482108 B2 | 12/2003 |
| JP | 2005261512 A | 9/2005 |
| JP | 2005319056 A | 11/2005 |
| JP | 4190252 B2 | 12/2008 |
| JP | 4199534 B2 | 12/2008 |
| JP | 4812515 B2 | 11/2011 |
| JP | 2012075473 A | 4/2012 |

(56) References Cited

FOREIGN PATENT DOCUMENTS

| | | |
|---|---|---|
| JP | 5399342 B2 | 1/2014 |
| JP | 6251808 B2 | 12/2017 |
| WO | 2012075131 A1 | 6/2012 |
| WO | 2015080694 A1 | 6/2015 |
| WO | 2019226307 A1 | 11/2019 |
| WO | 2020014376 A1 | 1/2020 |

* cited by examiner

ENDOSCOPE AIR/WATER FLUSH ADAPTOR AND METHOD

RELATED APPLICATIONS

This application claims the benefit of priority under 35 U.S.C. § 119 to U.S. Provisional Application No. 62/872,887, titled "Endoscope Air/Water Flush Adaptor and Method", filed on Jul. 11, 2019, the entirety of which is incorporated herein by reference.

FIELD

The present disclosure relates generally to the field of medical devices. In particular, the present disclosure relates to medical devices, systems and methods for air/water and flushing valves.

BACKGROUND

Following an endoscopic procedure, the endoscope and associated equipment are cleaned and/or reprocessed to prevent the spread of infection in a subsequent medical procedure with a different patient. A pre-cleaning step when using conventional endoscopic systems involves flushing air through the air lines and flushing water through the water lines using a procedural endoscopic valve. In some endoscopic systems, the air/water procedural endoscopic valve (which directs air and water from source equipment through respective air and water channels of the endoscope) is replaced with an air/water pre-cleaning valve, which diverts clean water from the source equipment through the air and water channel to flush away any procedural debris that may have entered the air or water channels. In addition to requiring the additional and time-consuming step of replacing the procedural valve with the air/water pre-cleaning valve, each valve must be individually tracked and reprocessed between each procedure.

It with these considerations in mind that a variety of advantageous medical outcomes may be realized by the devices, systems and methods of the present disclosure.

SUMMARY

In one aspect, the present disclosure relates to an endoscopic valve comprising a valve stem. The valve stem may comprise a proximal channel with a proximal opening and a distal channel with a distal opening. The proximal and distal channels may define a contiguous channel. A first port may be formed within a sidewall of the valve stem and may be in fluid communication with the proximal channel. A second port may be formed within the sidewall of the valve stem and may be in fluid communication with the proximal channel. A first seal may be disposed around an outer surface of the valve stem and distal to the first port. A second seal may be disposed around the outer surface of the valve stem and distal to the second port. A third seal may be disposed around the outer surface of the valve stem and distal to the second seal. A gating member may be slidably disposed within the proximal channel. The gating member may be configured to move between a first position in sealing contact with the first port and a second position in sealing contact with the second port. A lumen may extend through the gating member. A valve insert may be disposed between the proximal and distal channels.

In the described and other embodiments, a modular attachment may be insertable into the proximal channel of the valve stem and may move the gating member from the first position to the second position and may move the valve insert from a first position to a second position. The valve stem may be movable between a first configuration and a second configuration within a housing of an endoscope. The housing may comprise an air outlet port formed within a sidewall of the housing. An air inlet port may be formed within the sidewall of the housing and distal to the air outlet port. A water outlet port may be formed within the sidewall of the housing and distal to the air inlet port. A water inlet port may be formed within the sidewall of the housing and distal to the water outlet port. In the first configuration, air may be flowable from a processing system through the air inlet port and into the valve stem, and water may be flowable from the processing system through the water inlet port, into the valve stem and through the water outlet port. The air may be flowable through a proximal opening of the valve stem into the atmosphere. The air may be flowable through the air outlet port when a proximal opening of the valve stem is blocked. The valve stem may be movable between a first configuration, a second configuration and a third configuration within the housing of the endoscope. In the first configuration, air may be flowable from a processing system through the air inlet port and into the valve stem. The air may be flowable through a proximal opening of the valve stem and into the atmosphere. The air may be flowable through the air outlet port when a proximal opening of the valve stem is blocked. In the second configuration water may be flowable from a processing system through the water inlet port, into the valve stem and through the water outlet port. In the third configuration water may be flowable from a processing system through the water inlet port, into the valve stem and through the air outlet port, and water may be flowable from the processing system through the water inlet port, into the valve stem and through the water outlet port.

In another aspect, the present disclosure relates to an endoscopic valve comprising a valve stem. The valve stem may comprise an open proximal end and a closed distal end. A channel may extend between the proximal and distal ends. A first port may be form within a sidewall of the valve stem and may be in fluid communication with the channel. A second port may be formed within the sidewall of the valve stem distal to the first port and may be in fluid communication with the channel. A third port may be formed within the sidewall of the valve stem distal to the second port and may be in fluid communication with the channel. A first seal may be disposed around an outer surface of the valve stem and proximal to the first port. A second seal may be disposed around the outer surface of the valve stem between the first and second ports. A third seal may be disposed around the outer surface of the valve stem between the second and third port. A fourth seal may be disposed around the outer surface of the valve stem distal to the third port. An inner member may be movably disposed within the channel.

In the described and other embodiments, the inner member may comprise an open proximal end and a closed distal end. A lumen may extend between the proximal and distal ends. A first opening may be formed within a sidewall of the inner member and may be in fluid communication with the lumen at a proximal portion of the inner member. A second opening may be formed within the sidewall of the inner member and may be in fluid communication with the lumen at a distal portion of the inner member. A fifth seal may be disposed around an outer surface of the inner member and proximal to the first opening. A sixth seal may be disposed around the outer surface of the inner member and distal to the fifth seal and the first opening. A seventh seal may be disposed around the outer surface of the inner member and distal to the sixth seal and the first opening. An eighth seal may be disposed around the outer surface of the inner member and distal to the seventh seal and the first opening. A ninth seal may be disposed around the outer surface of the inner member and distal to the eighth seal and the second opening. An expandable member may extend through the sidewall of the inner member. The inner member may be configured to move the expandable member from a first configuration to a second configuration.

In yet another aspect, the present disclosure relates to an endoscopic system comprising a housing disposable within an endoscope handle. A length of tubing may extend from the endoscope handle to a processing system. An insertion tube may extend from the endoscope handle. An endoscopic valve may be movable between a first configuration and a second configuration within the housing. The endoscopic valve may comprise a valve stem. A first air channel and a first water channel may extend from the processing system to the housing through the length of tubing. A second air channel and a second water channel may extend from the housing through the insertion tube. In the first and second configurations air may be flowable from the processing system through the first air channel and into the valve stem, and water may be flowable from the processing system through the first water channel, into the valve stem and through the second water channel. The air may be flowable through a proximal opening of the endoscopic valve into the atmosphere. The endoscopic valve may be movable between a first configuration, a second configuration and a third configuration within the housing. In the third configuration water may flowable from the processing system through the first water channel, into the valve stem and through the second air channel, and water may be flowable from the processing system through the first water channel, into the valve stem and through the second water channel.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1A:
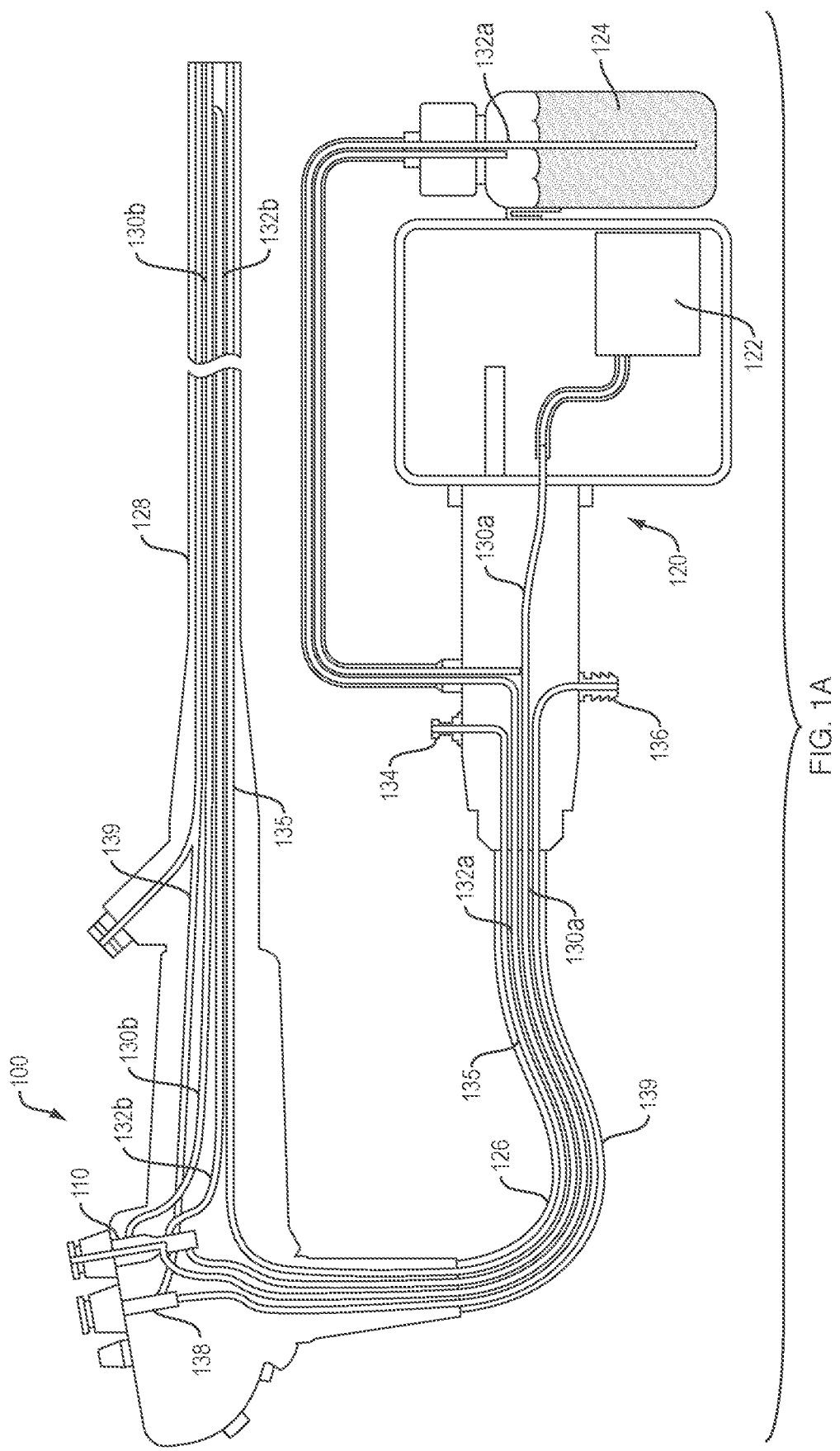
FIGS. 1A-1B provide perspective views of an endoscopic system (FIG. 1A), including an endoscopic valve housing (FIG. 1B).

Referring to FIG. 1A, in one embodiment, an endoscopic system may include an endoscope handle 100 attached to a processing system 120 by a length of tubing 126 (e.g., universal cord, umbilicus cable, etc.). The processing system 120 may include an air source 122 (e.g., air pump, etc.), a water source 124 (e.g., fluid source, etc.), a water-jet connector 134 and a suction connector 136. An insertion tube 128, e.g., configured to be inserted into a patient, may extend from a distal portion of the endoscope handle 100. A first air channel 130a may extend from the air source 122, through the length of tubing 126, to a housing 110 (e.g., valve cylinder, air/water port, etc.) within the endoscope handle 100, and a first water channel 132a may extend from the water source 124, through the length of tubing 126, to the housing 110. A second air channel 130b may extend from the housing 110 through the insertion tube 128, and a second water channel 132b may extend from the housing 110 through the insertion tube 128. In various embodiments, a distal end of the second air channel 130b may include an opening contiguous with an opening at a distal end of the insertion tube 128. In various additional embodiments, a distal end of the second water channel 132b may be fluidly connected to the second air channel 130b proximal to the distal end of the insertion tube 128. The housing 110 may be removably attachable to the endoscope handle 100 and in some embodiments may comprise a valve, so that when attached, air, water, suction, or combinations thereof may be deliverable to a patient and controllable by the respective valve(s).

In various embodiments, a water-jet channel 135 may extend through the length of tubing 126 and the insertion tube 128. A first (e.g., proximal) end of the water-jet channel may be fluidly attached to the water-jet connector 134, and a second (e.g., distal) end of the water-jet channel may include an opening contiguous with an opening at a distal end of the insertion tube 128, e.g., to deliver a water-jet into the patient. In various additional embodiments, a biopsy/suction channel 139 may extend through the tubing 126, connect to a suction valve 138 within the endoscope handle 100, and extend through the insertion tube 128. A first (e.g., proximal) end of the biopsy/suction channel 139 may be fluidly attached to the suction connector 136, and a second (e.g., distal) end of the biopsy/suction channel 139 may include an opening contiguous with an opening at a distal end of the insertion tube 128 e.g., to provide suction of fluids, e.g., liquids and/or gases, within the patient.

Figure 1B:
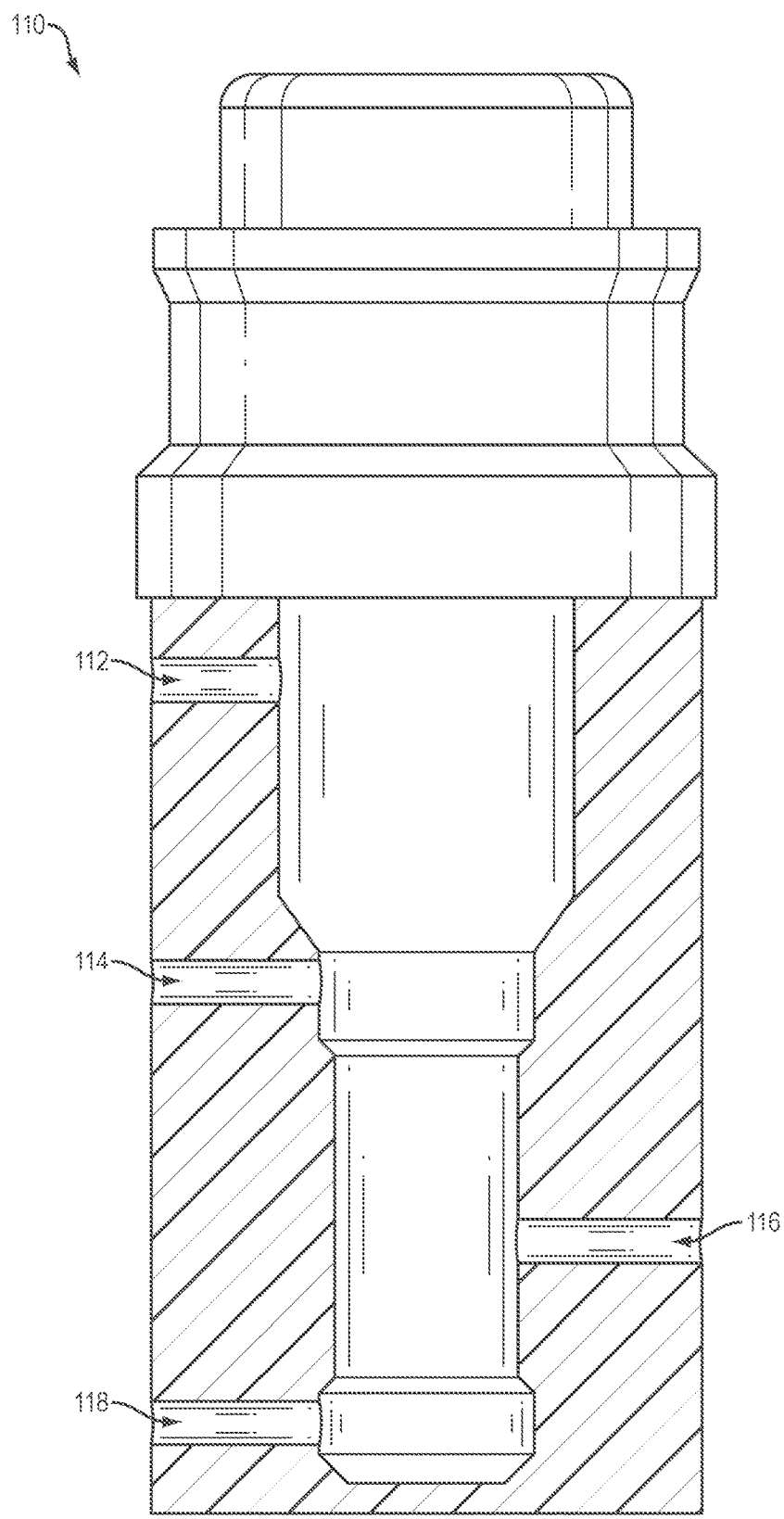

Referring to FIG. 1B, in one embodiment, the housing 110 may include an air outlet port 112, an air inlet port 114, a water outlet port 116 and a water inlet port 118 formed within (e.g., extend through) different respective portions/sections of a sidewall of the housing 110. For example, the air outlet port may be proximal to the air inlet port, the air inlet port may be proximal to water outlet port and the water outlet port may be proximal to the water inlet port. In various embodiments, the air outlet port 112 may be configured to align with (e.g., fluidly connected to, in fluid communication with, etc.) a proximal end of the second air channel extending through the insertion tube 128, the air inlet port 114 may be configured to align with a distal end of the first air channel extending through the length of tubing 126, the water outlet port 116 may be configured to align with a proximal end of the second water channel extending through the insertion tube 128 and the water inlet port 118 may be configured to align with a distal end of the first water channel extending through the length of tubing 126.

Referring to FIGS. 2A-2D, in one embodiment, an endoscopic system of the present disclosure may include an endoscopic valve 200 (e.g., air/water valve, etc.) disposable within a housing 110 of an endoscope handle 100 (FIGS. 1A-1B). In various embodiments, the endoscopic valve 200 may be configured to move (e.g., switch) between a first configuration (e.g., procedural configuration, medical procedure configuration, etc.) and a second configuration (e.g., post-operative/post-procedural pre-cleaning configuration).

Figure 2A:
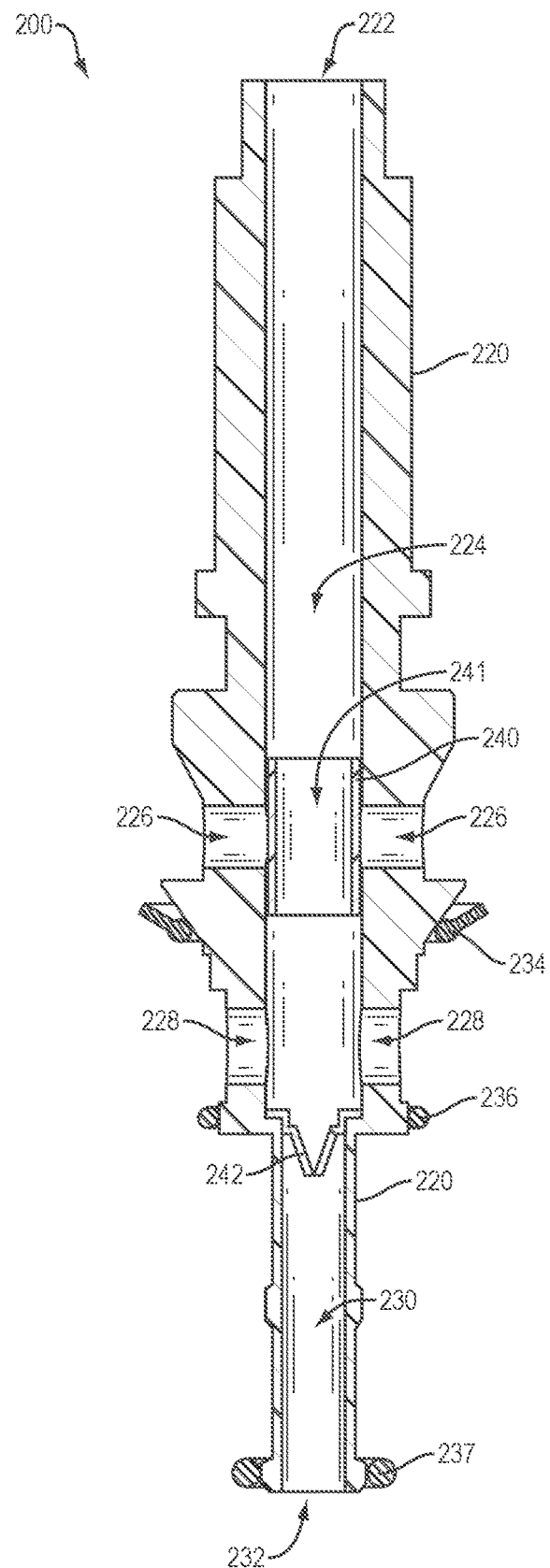
FIGS. 2A-2E provide perspective views of an endoscopic valve, according to one embodiment of the present disclosure.
Figure 2B:
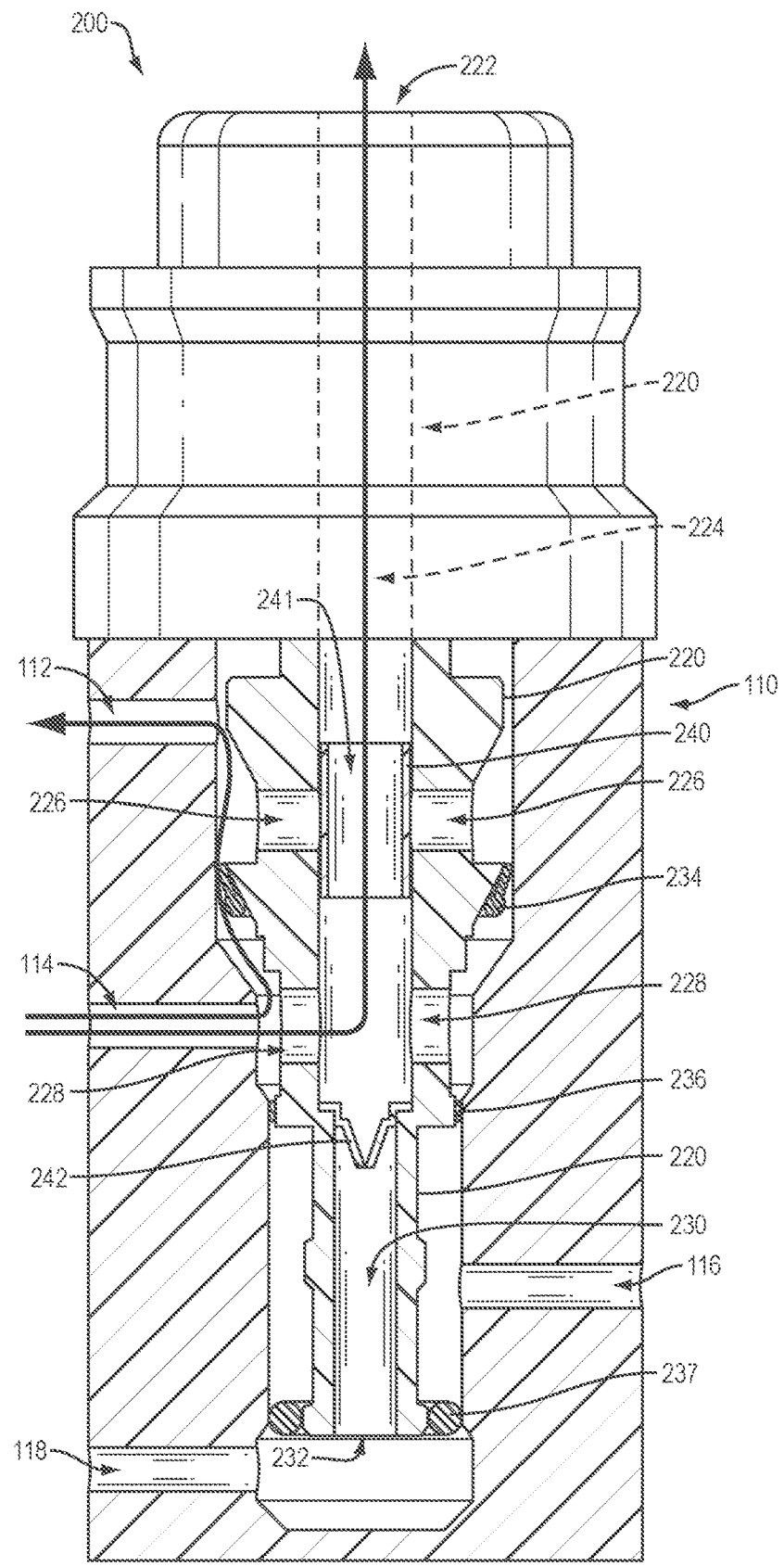

Referring to FIGS. 2A-2B, in one embodiment, the endoscopic valve 200 may include a valve stem 220 defining a proximal channel 224 (e.g., air vent channel) with a proximal opening 222 and a distal channel 230 (e.g., internal channel) with a distal opening 232. The proximal and distal channels 224, 230 may be co-extensive to define a contiguous channel through a full length of the valve stem 220. In various embodiments, at least a portion of the valve stem comprising the proximal channel 224 may extend beyond (e.g., outside) the housing 110 of the endoscope handle 100.

In one embodiment, a first port 226 (e.g., proximal port) and a second port 228 may be formed within (e.g., extend through) different respective portions/sections of a sidewall of the valve stem 220 and in fluid communication with the proximal channel 224. The first port 226 may be substantially aligned with the air outlet port 112 of the housing 110, and the second port 228 may be substantially aligned with the air inlet port 114 of the housing 110. A first seal 234 (e.g., one-way seal, O-ring, sealing member, enlarged portion, etc.) may be disposed around an outer surface of the valve stem 220 (e.g., a full circumference of the valve stem) between the first and second ports 226, 228. A second seal 236 may be disposed around an outer surface of the valve stem 220 (e.g., a full circumference of the valve stem) distal to the second port 228. A third seal 237 may be disposed around an outer surface of the valve stem 220 (e.g., a full circumference of the valve stem) proximal to the distal opening 232.

In various embodiments, the first seal 234 may be a single-direction seal (or one-way seal) configured to sealingly contact an inner wall of the housing 110 between the air outlet port 112 and air inlet port 114 and proximal to the second port 228. The second seal 236 may be configured to sealingly contact an inner wall of the housing 110 distal to the air inlet port 114. In addition, or alternatively, the first and second seals 234, 236 may be configured to seal a space between the housing 110 and the valve stem 220 around (e.g., 360°) the air inlet port 114 of the housing 110 and the first port 226 of the valve stem 220. The third seal 237 may be configured to sealingly contact an inner wall of the housing 110 proximal to the water inlet port 118 and distal to the water outlet port 116 (e.g., between the water inlet port 118 and water outlet port 116).

A gating member 240 may be movably (e.g., slidably, etc.) disposed within a distal portion of the proximal channel 224. A lumen 241 may extend through a full length of the gating member, e.g., to allow the flow of water/air therethrough. The gating member 240 may be configured to move from a first position (e.g., proximal position) substantially adjacent to and in sealing contact with the first port 226 (FIG. 2A) and a second position (e.g., distal position) substantially adjacent to and in sealing contact with the second port 228 (FIG. 2E, discussed below). In various embodiments, the sealing contact between the gating member 240 and the first or second port 226, 228 may block/prevent the respective flow of air or water into/through the proximal channel 224 (discussed below).

A valve insert 242 (e.g., duck-bill valve) may be disposed between (e.g., at an approximate junction of) the proximal and distal channels 224, 230 and configured to move between a first position (e.g., closed) and a second position (e.g., open).

Referring to FIG. 2B, with the endoscopic valve 200 in the first configuration, e.g., non-depressed within the housing 110 and the gating member 240 in the first position and in sealing contact with the first port 226 and the valve insert 242 in the first (e.g., closed) position, air may flow from the processing system 120, through the first air channel 130a, through the air inlet port 114 of the housing and the second port 228 of the valve stem 220, through the lumen of the gating member 240 and the proximal channel 224 and into the atmosphere through proximal opening 222 (see arrow in FIG. 2B flowing from the air inlet port 114 to the proximal opening 222). In addition, with the endoscopic valve 200 in the first configuration, the third seal 237 may sealingly contact an inner wall of the housing 110 such that water may not flow from the processing system 120, through the first water channel 132a, through the water inlet port 118 and water outlet port 116 of the housing and through the second water channel 132b into the patient. Additionally, water may be prevented from flowing through the distal opening 232 and the distal channel of the valve stem 220 proximally beyond the valve insert 242 (e.g., with the valve insert 242 in the first position) and into the proximal channel.

In one embodiment, with the endoscopic valve 200 in the first configuration and with the proximal opening 222 of the valve stem 220 closed (e.g., blocked/sealed by a thumb or forefinger of a medical professional), air may flow from the processing system 120, through the first air channel 130a, through the air inlet port 114 of the housing, around the first seal 234 (e.g., blowing by the single-direction seal when a threshold level of air pressure is exceeded), through the air outlet port 112 and second air channel 130b and into the patient (see arrow in FIG. 2B flowing from the air inlet port 114 to the air outlet port 112).

Figure 2C:
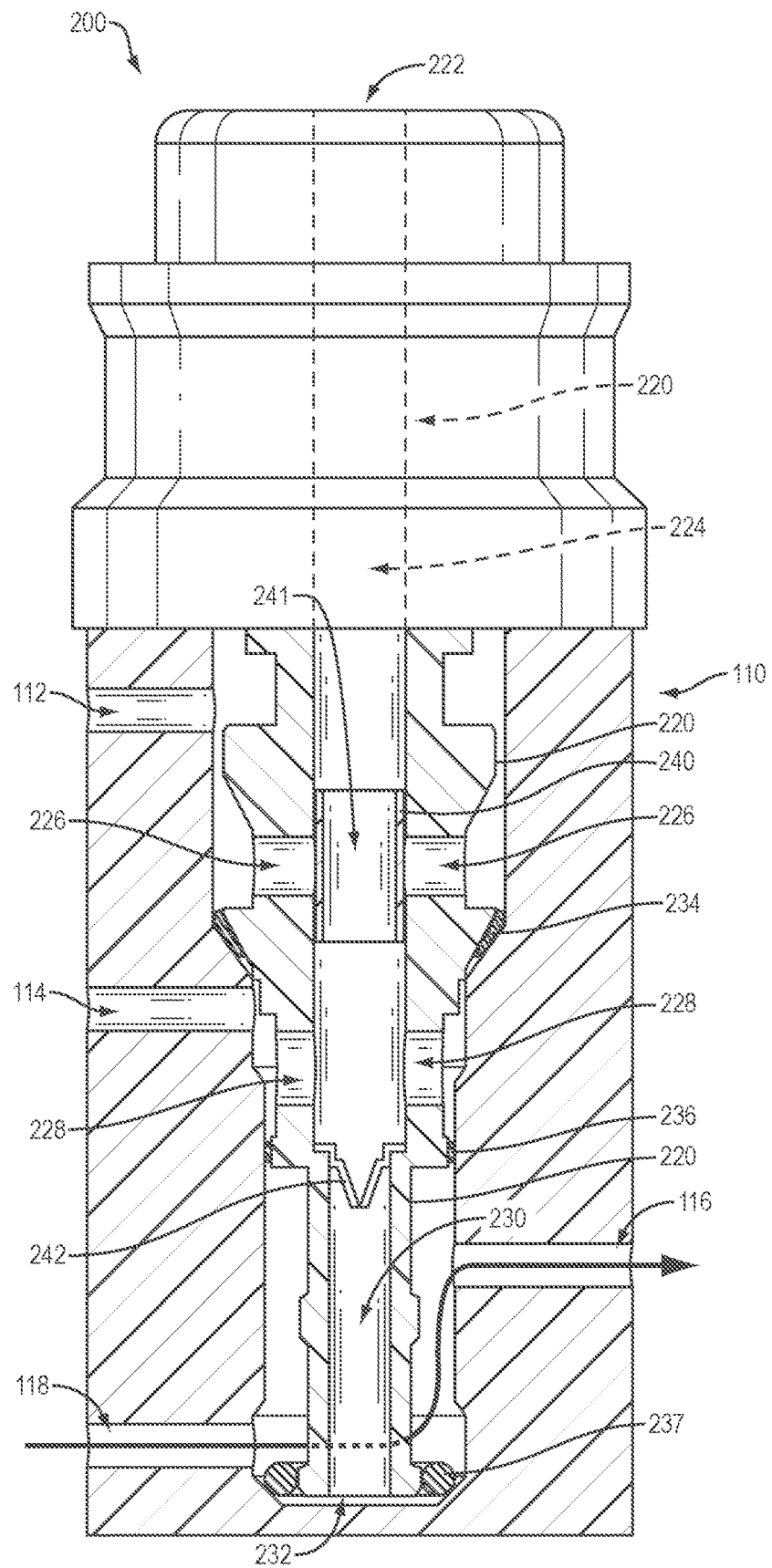

Referring to FIG. 2C, with the endoscopic valve 200 in a second configuration, e.g., depressed within the housing 110 and the gating member 240 in the first position, the first seal 234 may be compressed against an inner wall of the housing (e.g., a slanted or angled surface of the housing), such that air cannot flow past the first seal 234 and through the air outlet port 112.

In addition, with the endoscopic valve 200 in the second configuration, the third seal 237 may not sealingly contact an inner wall of the housing such that water may flow from the processing system 120, through the first water channel 132a, through the water inlet port 118 of the housing 110, around an outer surface of the valve stem 220 (e.g., distal to the second seal 236), through the water outlet port 116 and second water channel 132b and into the patient (see arrow in FIG. 2C flowing from the water inlet port 118 to the water outlet port 116). The second seal 236 may sealingly contact an inner wall of the housing 110 proximal to the water outlet port 116 such that water may not flow proximally beyond the second seal 236 (e.g., through the air inlet port 114). Water may be prevented from flowing through the distal opening 232 and the distal channel 230 of the valve stem 220 proximally beyond the closed valve insert 242 and into the proximal channel 224.

Figure 2D:
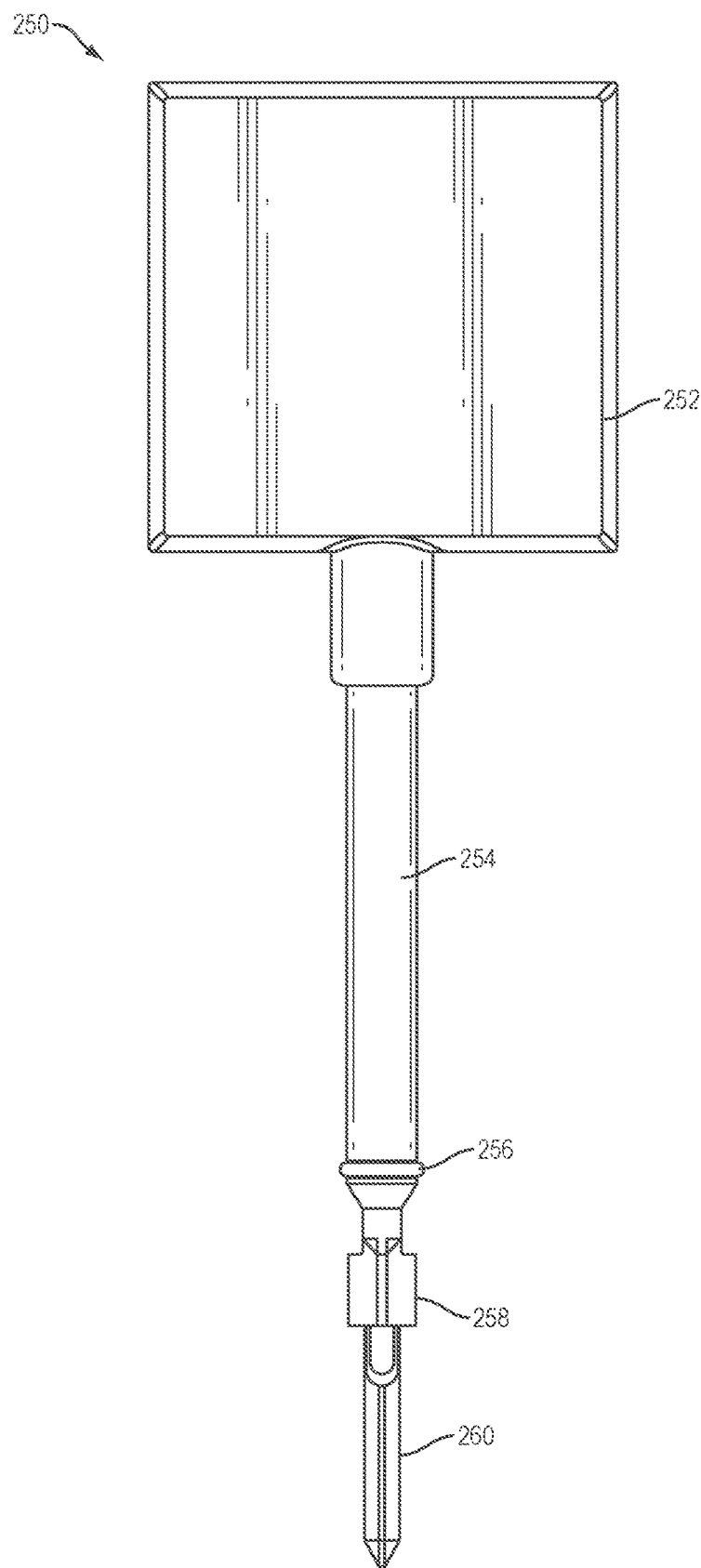
Figure 2E:
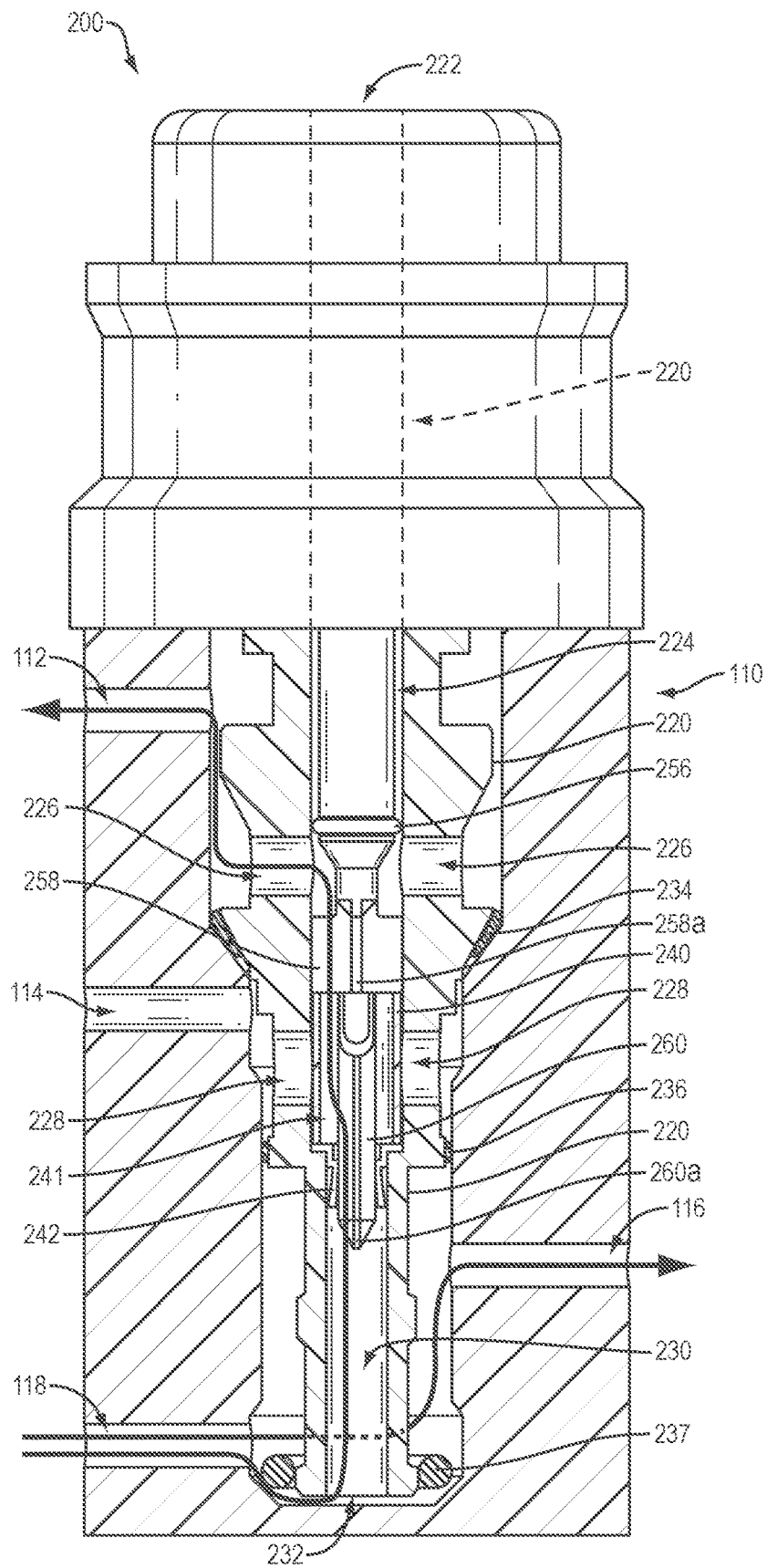

Referring to FIG. 2D, in one embodiment, an endoscopic system of the present disclosure may further include a modular attachment 250 insertable into the proximal channel 224 of the valve stem 220 to move the endoscopic valve 200 from the first configuration to the second configuration. In various embodiments, the modular attachment 250 may include a handle 252, a shaft 254 attached to or integrally formed with the handle 252, an engagement member 258 (e.g., flange, etc.) attached to or integrally formed with the shaft 254 and a penetrating member 260 attached to or integrally formed with the engagement member 258. A seal 256 may be disposed around an outer circumference of the shaft 254 proximal to the engagement member 258. The engagement member 258 and the penetrating member 260 may each include a series of ribs disposed along a longitudinal axis of the modular attachment 250. In various embodiments, the engagement member 258 may include a cross-sectional outer dimension larger than a corresponding inner dimension of the lumen 241 of the gating member 240 and the penetrating member 260 may include a cross-sectional outer dimension smaller than the outer dimensions of the engagement member 258 and the lumen 241 of the gating member 240.

Referring to FIG. 2E, upon completion of a medical procedure, the insertion tube 128 may be removed from within the patient. The modular attachment 250 may then be inserted into the proximal channel 224 of the valve stem 220 to move the endoscopic valve 200 from the first to second configuration. In one embodiment, the modular attachment 250 may be insertable into the proximal channel 224 of the valve stem 220 such that a distal end of engagement member 258 contacts a proximal end of the gating member 240 to move the gating member 240 from the first position (e.g., in sealing contact with the first port 226) to the second position (e.g., in sealing contact with the second port 228). The penetrating member 260 may extend through the lumen 241 of the gating member 240 such that a distal end of the penetrating member 260 penetrates (e.g., passes through) through the valve insert 242 to move the valve insert 242 from the first (e.g., closed) to second (e.g., open) position. In various embodiments, the ribs of the engagement member 258 and penetrating member 260 may be configured to allow water to flow along/around an outer surface of the modular attachment 250 and through the distal and proximal channels 230, 224 of the valve stem 220. In addition, the seal 256 may be configured to sealingly contact an inner wall of the proximal channel 224 of the valve stem 220 proximal to the first port 226, e.g., to block/prevent the flow of water through the proximal channel 224 proximally beyond the first port 226.

In one embodiment, the sealing contact between the gating member 240 and the second port 228 may block/prevent air flow from the processing system 120 from entering the proximal channel 224 through the air inlet port 114, thereby preventing/blocking the flow of air through the proximal opening 222 and/or the air outlet port 112. In addition, water may flow from the processing system 120, through the first water channel 132a, through the water inlet port 118 of the housing 110, around an outer surface of the valve stem 220 (e.g., distal to the second seal 236), through the water outlet port 116 and second water channel 132b (see arrow in FIG. 2E flowing from the water inlet port 118 to the water outlet port 116). Water may also flow from the processing system 120, through the first water channel 132a, through the water inlet port 118 of the housing 110, through the distal opening 232 and the distal channel 230 of the valve stem 220, through the proximal channel 224 (e.g., around the outer surfaces of the penetrating member 260, engagement member 258 and shaft 254 distal to the seal 256 of the modular attachment 250) through the first port 226 and through the air outlet port 112 and second air channel 130b (see arrow in FIG. 2E flowing from the water inlet port 118 to the air outlet port 112). In various embodiments, the gating member 240 and valve insert 242 may return to their respective first positions when the modular attachment 250 is removed from the proximal channel 224 of the valve stem 220. For example, the gating member may be biased (e.g., spring-loaded, etc.) to return to the first position when the modular attachment is removed.

Referring to FIGS. 3A-3D, in one embodiment, an endoscopic system of the present disclosure may include an endoscopic valve 300 (e.g., air/water valve, etc.) disposable within a housing 110 of an endoscope handle 100 (FIGS. 1A-1B), as discussed above. The endoscopic valve 300 may include an inner member 340 movably (e.g., slidably, etc.) disposable within a valve stem 320. In various embodiments, the inner member 340 and valve stem 320 may be configured to move (e.g., switch) the endoscopic valve 300 between a first configuration (e.g., air-flow procedural configuration, medical procedure configuration, etc.), a second configuration (e.g., water-flow procedural configuration, medical procedure configuration, etc.) and a third configuration (e.g., post-operative/post-procedural pre-cleaning configuration). In one embodiment, the endoscopic valve 300 may be moved to the third configuration upon completion of a medical procedure and with the insertion tube 128 removed from within the patient for pre-cleaning.

In one embodiment, the valve stem 320 may include an open proximal end 322 (e.g., proximal opening), a closed distal end 324 (e.g., sealed distal end) and a channel 325 extending therebetween (e.g., through a full length of the valve stem). A first port 326 (e.g., proximal port, top port, etc.) may be formed within (e.g., extend through) a sidewall of the valve stem 320 and in fluid communication with the channel 325, a second port 328 (e.g., intermediate port, middle port, etc.) may be formed within (e.g., extend through) a sidewall of the valve stem 320 and in fluid communication with the channel 325 distal to the first port 326 and a third port 330 (e.g., distal port, bottom port, etc.) may be formed within (e.g., extend through) a sidewall of the valve stem 320 and in fluid communication with the channel 325 distal to the second port 328. A first seal 332 may be disposed around an outer surface of the valve stem 320 (e.g., a full circumference of the valve stem) proximal to the first port 326. A second seal 334 may be disposed around an outer surface of the valve stem 320 (e.g., a full circumference of the valve stem) distal to the first port 326 and proximal to the second port 328 (e.g., between the first and second ports 326, 328). In various embodiments, the second seal 334 may be a single-direction seal configured to move or fold from a sealed configuration (e.g., in contact with an inner wall of the housing 110) to an open configuration when a threshold level of air pressure is exceeded. A third seal 336 may be disposed around an outer surface of the valve stem 320 (e.g., a full circumference of the valve stem) distal to the second port 328 and proximal to the third port (e.g., between the second and third ports 328, 330). A fourth seal 338 may be disposed around an outer surface of the valve stem 320 (e.g., a full circumference of the valve stem) distal to the third port 330.

In one embodiment, the inner member 340 may include an open proximal end 342 (e.g., proximal opening), a closed distal end 344 (e.g., sealed distal end) and a lumen 345 extending therebetween (e.g., through a full length of the inner member 340). A first opening 346 (e.g., proximal opening, top opening, etc.) may be formed within (e.g., extend through) a sidewall of the inner member 340 and in fluid communication with the lumen 345 at a proximal end of the valve stem, and a second opening 348 (e.g., distal opening, bottom opening, etc.) may be formed within (e.g., extend through) a sidewall of the inner member 340 and in fluid communication with the lumen 345 at a distal end of the valve stem 320 distal to the first opening 346. A fifth seal 352 may be disposed around an outer surface of the inner member 340 (e.g., a full circumference of the valve stem) proximal to the first opening 346 and proximal to the first port 326 and the air outlet port 112. A sixth seal 354 may be disposed around an outer surface of the inner member 340 (e.g., a full circumference of the valve stem) distal to the first opening 346 and the fifth seal 352 and proximal to the first port 326 and the air outlet port 112 (e.g., between the first and second openings 346, 348). A seventh seal 356 may be disposed around an outer surface of the inner member 340 (e.g., a full circumference of the valve stem) distal to the first opening 346 and the sixth seal 354 (e.g., between the first and second openings 346, 348) and distal to the first port 326. An eighth seal 358 may be disposed around an outer surface of the inner member 340 (e.g., a full circumference of the valve stem) distal to the first opening 346 and the seventh seal 356 (e.g., between the first and second openings 346, 348) and proximal to the second port 32 and the air inlet port 114. A ninth seal 360 may be disposed around an outer surface of the inner member 340 (e.g., a full circumference of the valve stem) distal to the second opening 348 and the eighth seal 358 and distal to the second port 32 and the air inlet port 114.

Figure 3A:
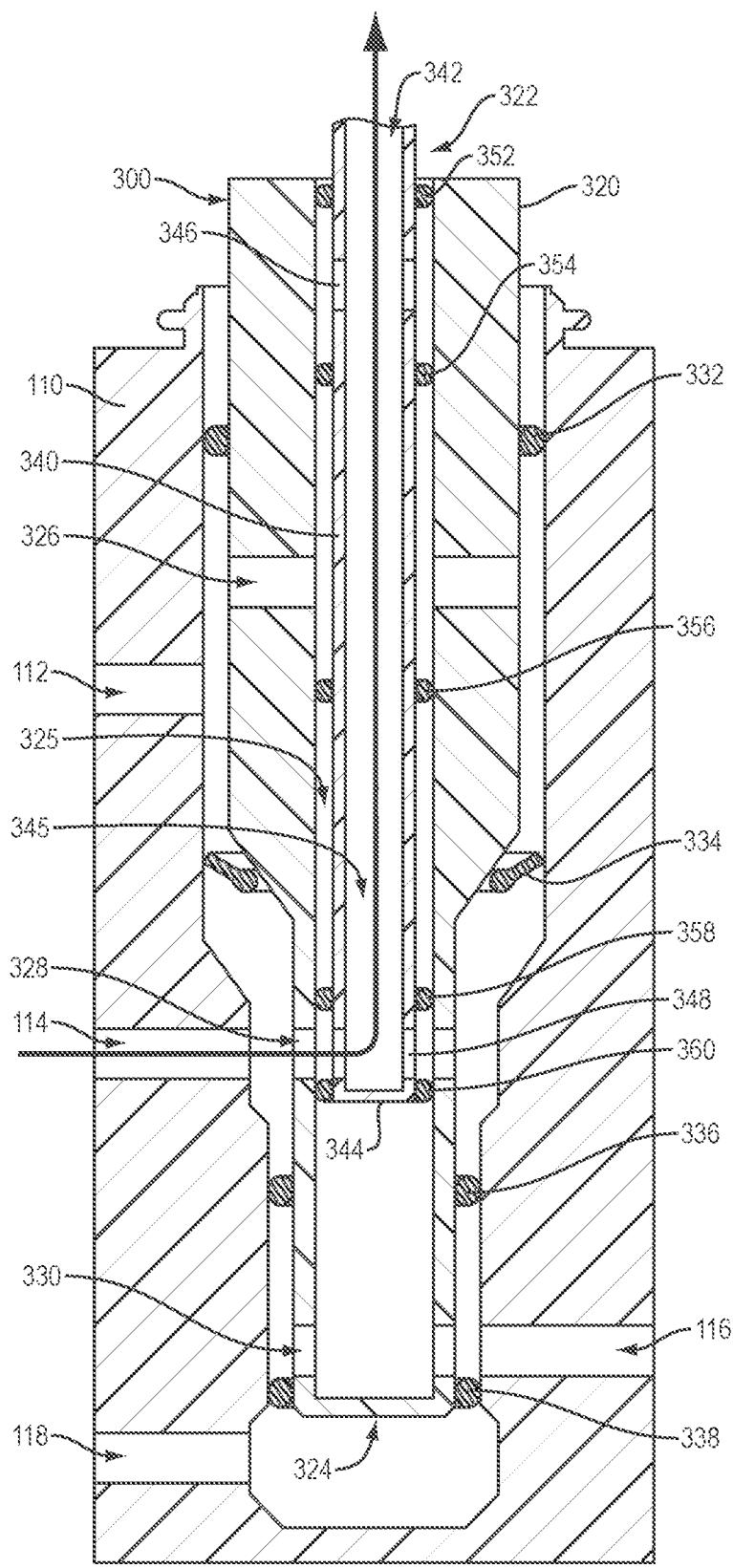
FIGS. 3A-3D provide perspective views of an endoscopic valve, according to one embodiment of the present disclosure.

Referring to FIG. 3A, with the endoscopic valve 300 in the first configuration, the valve stem 320 may not be depressed within the housing 110 (e.g., a distal end of the valve stem 320 is separated from a distal end of the housing 110 by a distance along a longitudinal axis) and the inner member 340 may not be depressed within the valve stem 320 (e.g., a distal end of the inner member 340 is separated from a distal end of the valve stem 320 by a distance along a longitudinal axis).

In the first configuration, air may flow from the processing system 120, through the first air channel 130a, through the air inlet port 114 of the housing 110, through the second port 328 of the valve stem 320, through the second opening 348 of the inner member 340 and through the lumen 345 and open proximal end 342 of the inner member 340 into the atmosphere (see arrow in FIG. 3A flowing from the air inlet port 114 to the open proximal end 342). In various embodiments, the direction of air flow may be controlled by the combined sealing capabilities of the various seals. For example, the second seal 334 may block/prevent the flow of air through the air outlet port 112 of the housing 110. The sealing contact between the fifth seal 352 and the inner surface of the channel 325 of the valve stem 320 may block/prevent the proximal flow of air through the first opening 346 of the inner member 340 and into the atmosphere. The sealing contact between the sixth seal 354 and the inner surface of the channel 325 of the valve stem 320 may block/prevent the distal flow of air through the first opening 346 of the inner member 340 and through first port 326 of the valve stem 320 into the air outlet port 112 of the housing 110. The sealing contact between the seventh and eighth seals 356, 358 may block/prevent the proximal flow of air through the second opening 348 of the inner member and through first port 326 of the valve stem 320 into the air outlet port 112 of the housing 110. The sealing contact between the ninth seal 360 and the inner surface of the channel 325 of the valve stem 320 may block/prevent the distal flow of air through second port 328 of the valve stem 320 into the water outlet port 116 of the housing 110. The sealing contact between the first seal 332 and an inner surface of the housing 110 may block/prevent the proximal flow of air through the air inlet port 114 into the atmosphere. The sealing contact between the third seal 336 and an inner surface of the housing 110 may block/prevent the distal flow of air from the air inlet port 114 through the third port 330 of the valve stem 320 and into the water outlet port 116 of the housing 110.

Figure 3B:
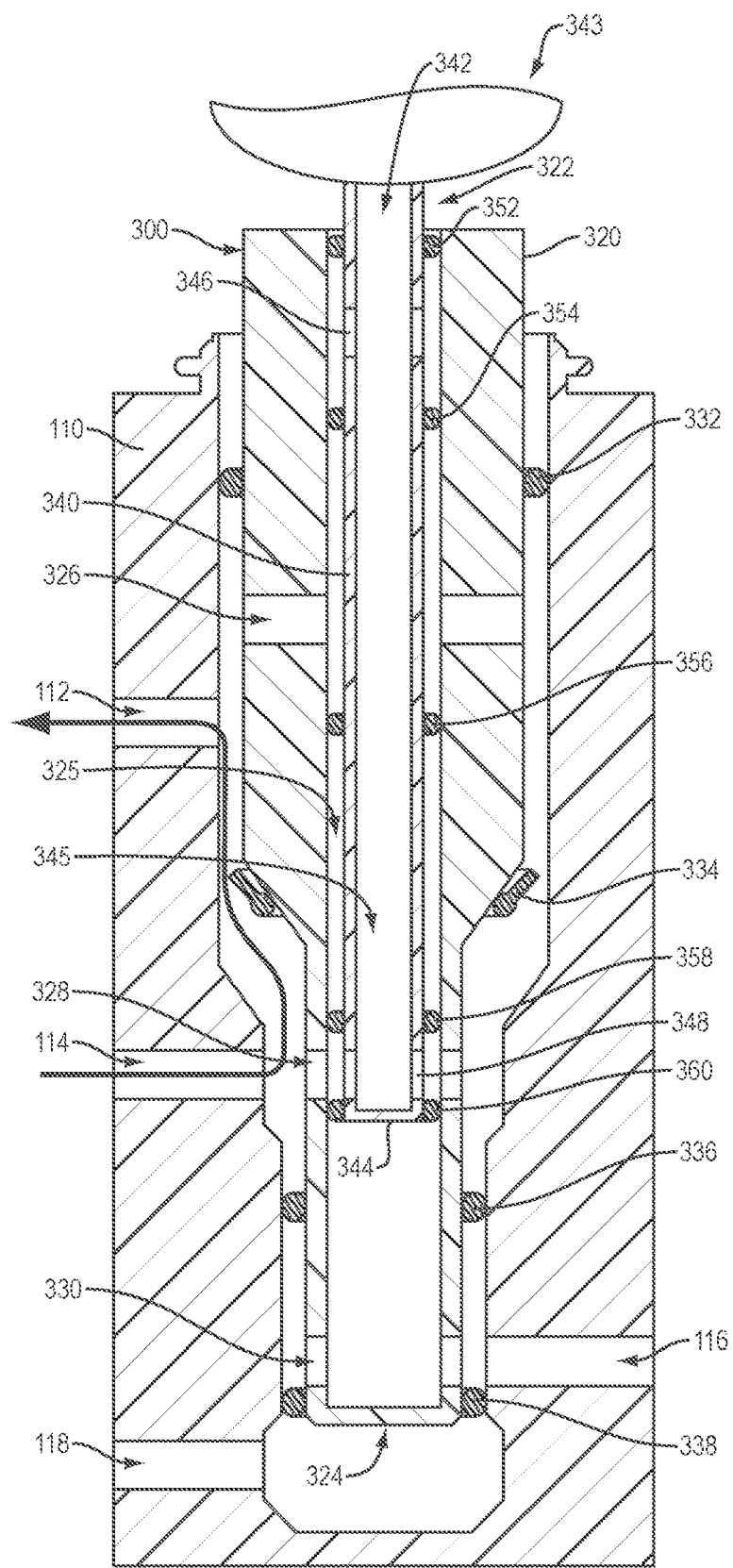

Referring to FIG. 3B, with the endoscopic valve 300 in the first configuration and the open proximal end 342 of the inner member blocked or otherwise obstructed (e.g., by a finger or thumb 343 of a medical professional), air may be diverted from exiting into the atmosphere and instead flow from the air inlet port 114, between the housing 110 and the valve stem 320 by blowing past the second seal 334 and through the air outlet port 112 and second air channel 130b and into the patient (see arrow in FIG. 3B flowing from the air inlet port 114 to the air outlet port 112).

In addition, in the first configuration, although water may flow from the processing system 120, through the first water channel 132a and through the water inlet port 118 of the housing 110, the water may be prevented from flowing through the water outlet port 116 and the second water channel 132b due to the sealing contact between the fourth seal 338 of the valve stem 320 and the inner surface of the housing 110.

Figure 3C:
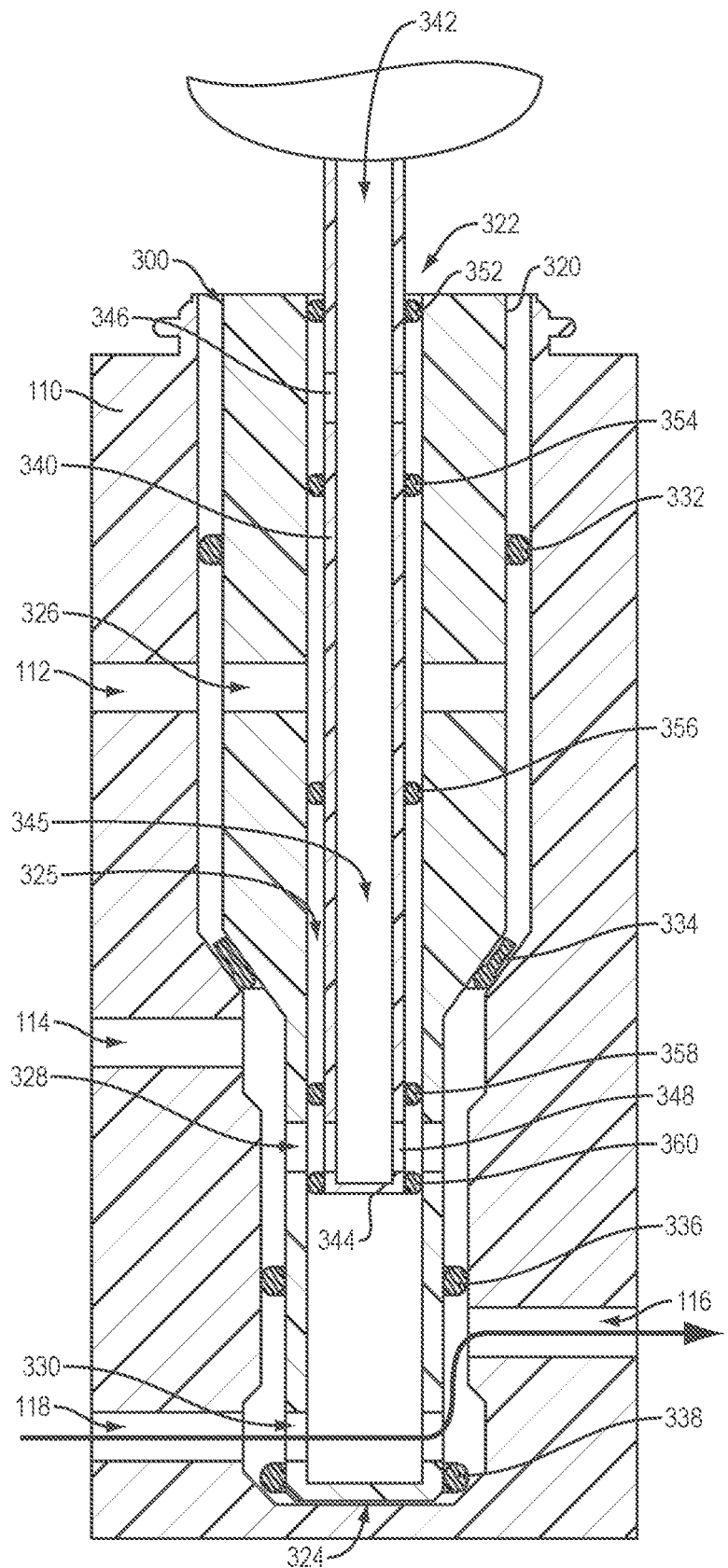

Referring to FIG. 3C, with the endoscopic valve in a second configuration, the valve stem 320 may be depressed (e.g., distally advanced) within the housing 110 (e.g., a distal end of the valve stem 320 is in contact with or substantially adjacent to a distal end of the housing 110) and the inner member 340 may move along with the valve stem 320 but is not depressed within (e.g., relative to) the valve stem 320 (e.g., a distal end of the inner member 340 is separated from a distal end of the valve stem 320 by a distance along a longitudinal axis).

In the second configuration the flow of air may be blocked. For example, air may flow from the processing system 120, through the housing 110, valve stem 320 and inner member 340 as discussed above (FIG. 3A), but the open proximal end 342 may be blocked or otherwise obstructed, e.g., by a finger or thumb of a medical professional, to block/prevent air flow into the atmosphere. In addition, the sealing contact between the second seal 334 and the inner surface of the housing 110 may block/prevent the proximal flow of air from the air inlet port 114, between the housing 110 and the valve stem 320, through the air outlet port 112 and second air channel 130b and into the patient. In various embodiments, the sealing contact between the remaining seals (e.g., first seal 332, third seal 336, fifth seal 352, sixth seal 354, seventh seal 356, eighth seal 358 and ninth seal 360) may block/prevent the respective flow of air and water as discussed above.

In addition, in the second configuration, water may flow from the processing system 120, through the first water channel 132a, through the water inlet port 118 of the housing 110, through the third port 330 of the valve stem 320, through the water outlet port 116 of the housing 110 and the second water channel 132b and into the patient (see arrow in FIG. 3C flowing from the water inlet port 118 to the water outlet port 116). The sealing contact between the third seal 336 of the valve stem 320 and the inner surface of the housing, and the sealing contact between the ninth seal 360 of the inner member 340 and the inner surface of the valve stem 320, may prevent the proximal flow of water beyond water outlet port 116.

Figure 3D:
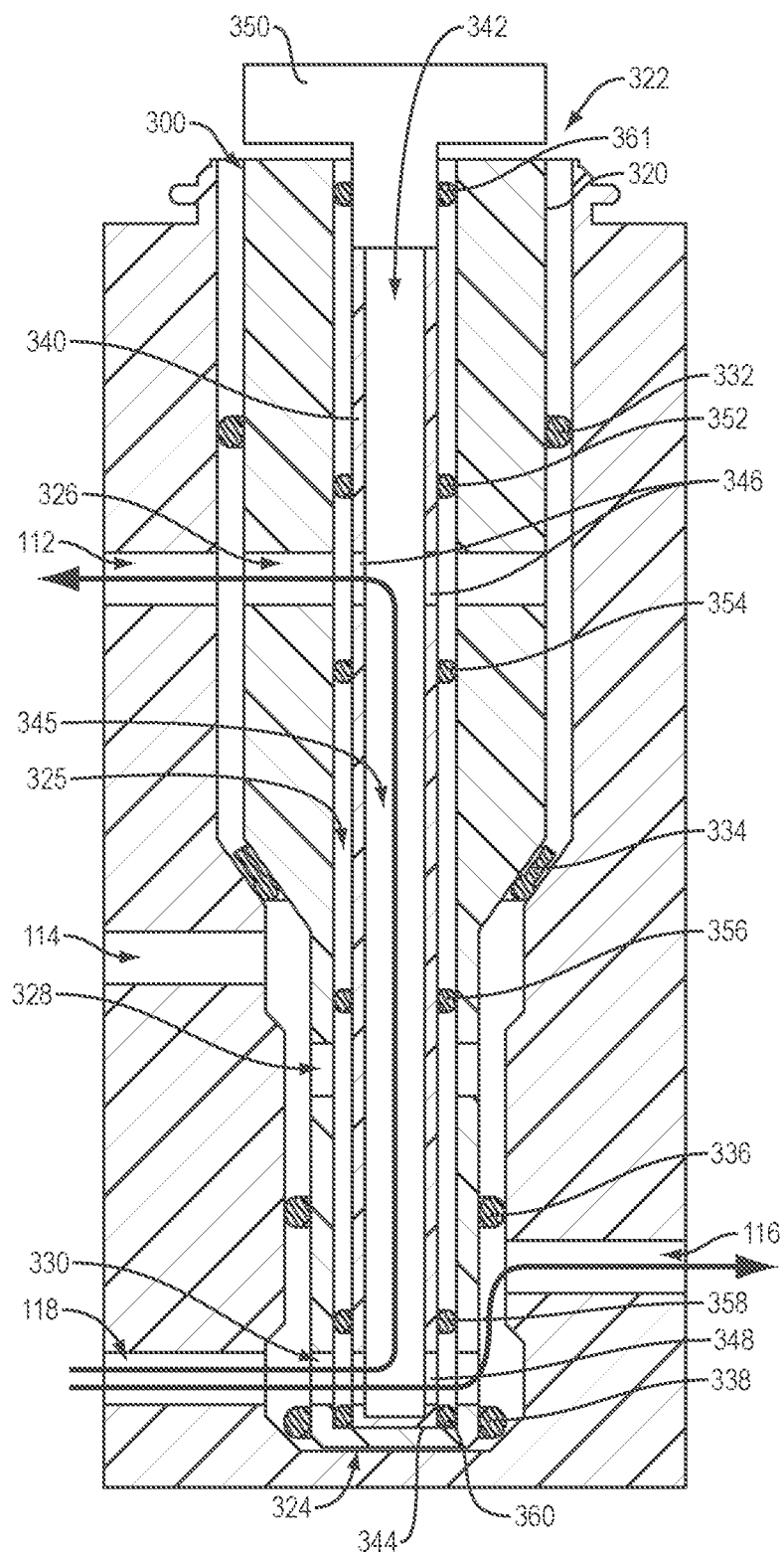

Referring to FIG. 3D, with the endoscopic valve in a third configuration, the valve stem 320 may be depressed (e.g., distally advanced) within the housing 110 (e.g., a distal end of the valve stem 320 is in contact with or substantially adjacent to a distal end of the housing 110) and the inner member 340 may be depressed within the valve stem 320 (e.g., a distal end of the inner member 340 is in contact with or substantially adjacent to a distal end of the valve stem 320). In one embodiment, a modular attachment 350 may be inserted (e.g., distally advanced) into/through the proximal opening 322 of the valve stem 320 to depress (e.g., distally advance) the inner member 340 within the valve stem 320. In various embodiments, the modular attachment may include a tenth seal 361 configured to sealingly contact the inner surface of the channel 325 of the valve stem 320 to block/prevent the flow of water through the open proximal end 342 of the inner member 340, e.g., to divert the flow of water through the first opening 346.

In the third configuration, air may flow from the processing system 120, through the first air channel 130a, through the air inlet port 114 of the housing 110 and through the second port 328 of the valve stem 320, but may be blocked from flowing proximally through the channel 325 of the valve stem 320, e.g., by the sealing contact between the seventh seal 356 and the inner surface of the channel 325, and may be blocked from flowing distally through the channel 325 of the valve stem 320 and through the second opening 348 of the inner member 340 e.g., by the sealing contact between the eighth seal 358. In addition, the sealing contact between the second and third seals 334, 336 and the inner surface of the housing 110 may block/prevent the proximal and distal flow of air from the air inlet port 114, between the housing 110 and the valve stem 320, through the air outlet port 112 (e.g. by second seal 334) and/or the water inlet port 118 (e.g., by the third seal 336).

In addition, in the third configuration, water may flow from the processing system 120, through the first water channel 132a, through the water inlet port 118 of the housing 110, through the third port 330 of the valve stem 320, through the second opening 348 of the inner member, through the water outlet port 116 of the housing 110 and through the second water channel 132b (see arrow in FIG. 3D flowing from the water inlet port 118 to the water outlet port 116). As above, the sealing contact between the third seal 336 of the valve stem 320 and the inner surface of the housing 110 may prevent the proximal flow of water beyond water outlet port 116 between the housing 110 and the valve stem 320.

In addition, in the third configuration, water may also flow from the processing system 120, through the first water channel 132a, through the water inlet port 118 of the housing 110, through the third port 330 of the valve stem 320, through the second opening 348 and lumen 345 of the inner member 340, through the first opening 346 of the inner member 340, through the first port 326 of the valve stem 320, through the air outlet port 112 of the housing 110 and through second air channel 130b (see arrow in FIG. 3D flowing from the water inlet port 118 to the air outlet port 112).

Figure 4A:
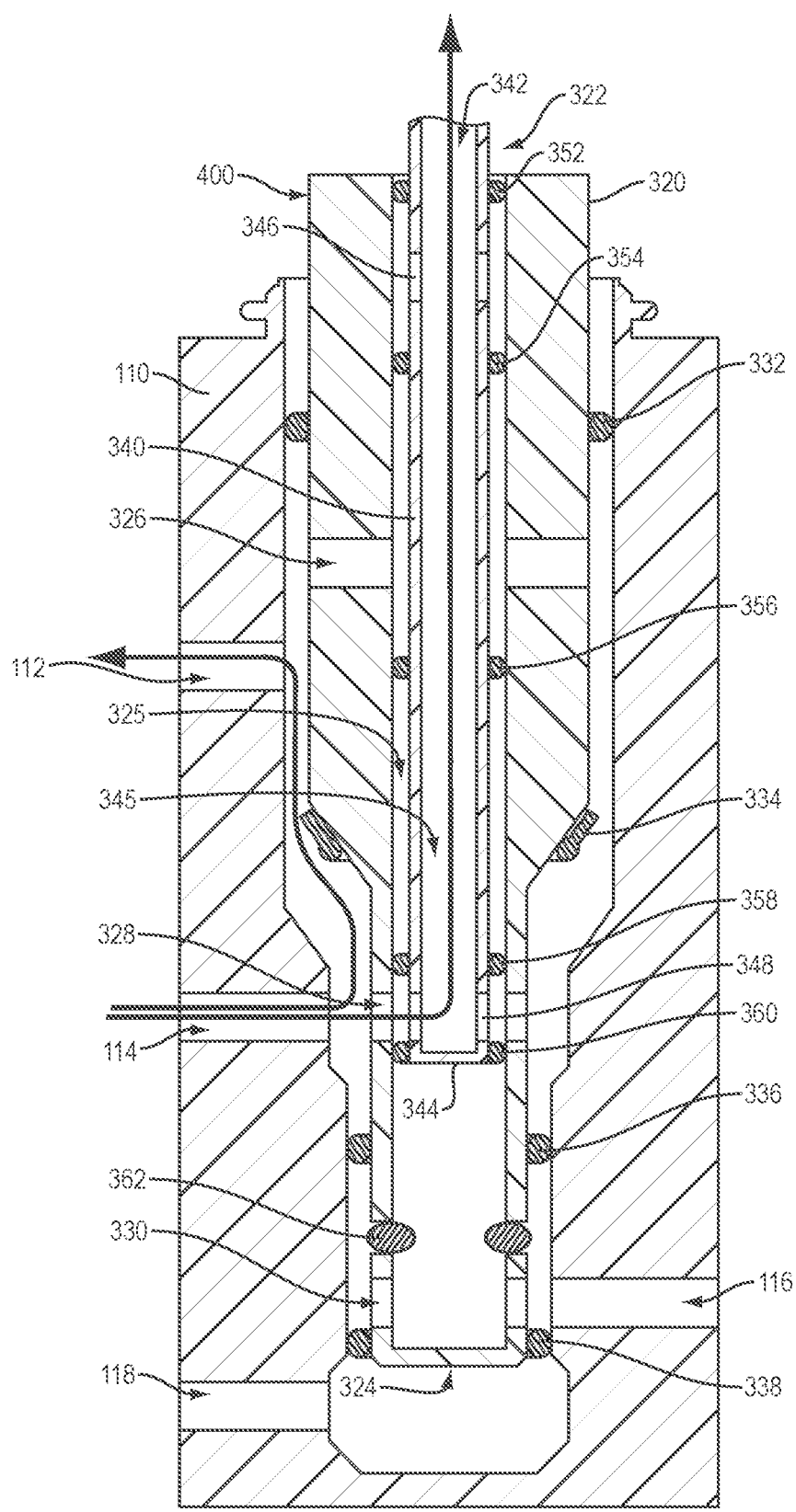
FIGS. 4A-4C provide perspective views of an endoscopic valve, according to one embodiment of the present disclosure.
Figure 4B:
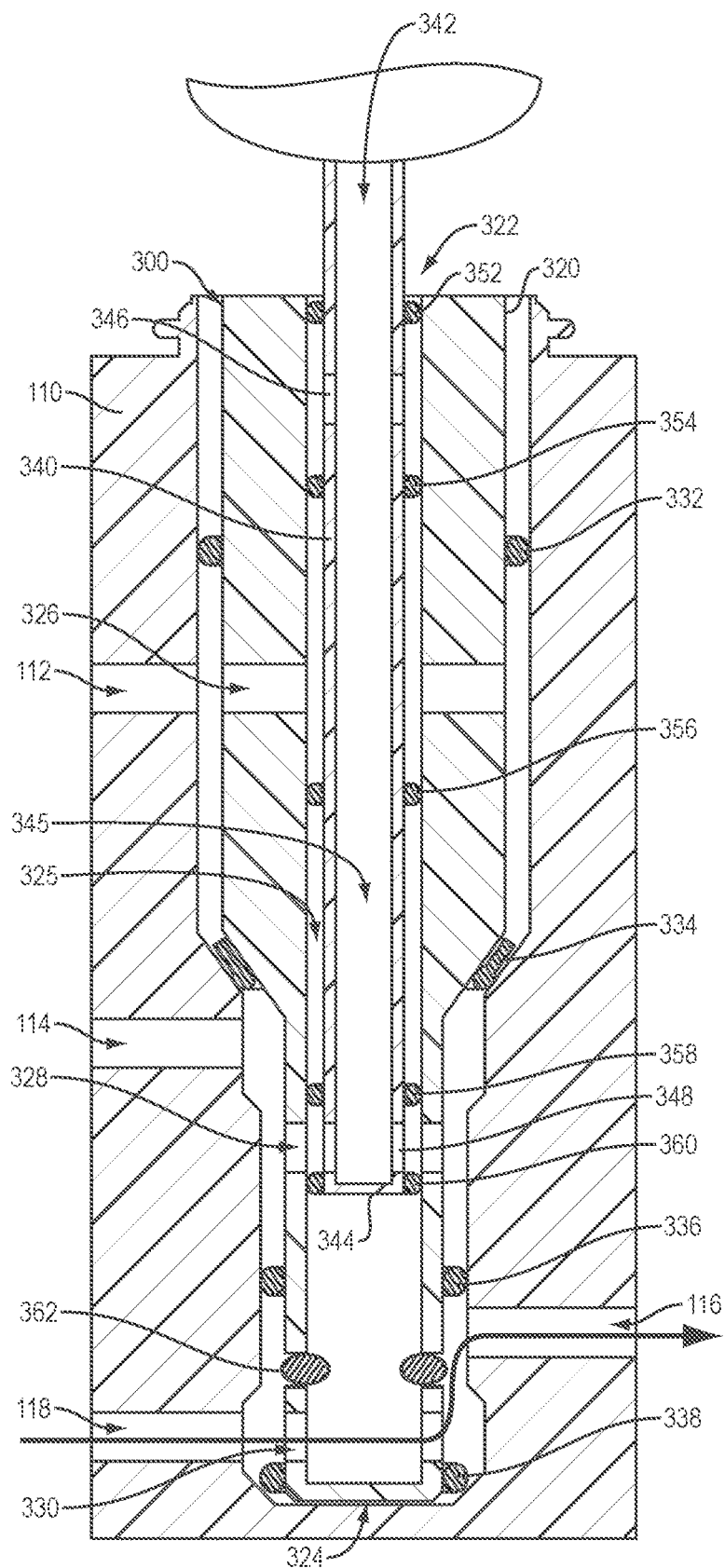
Figure 4C:
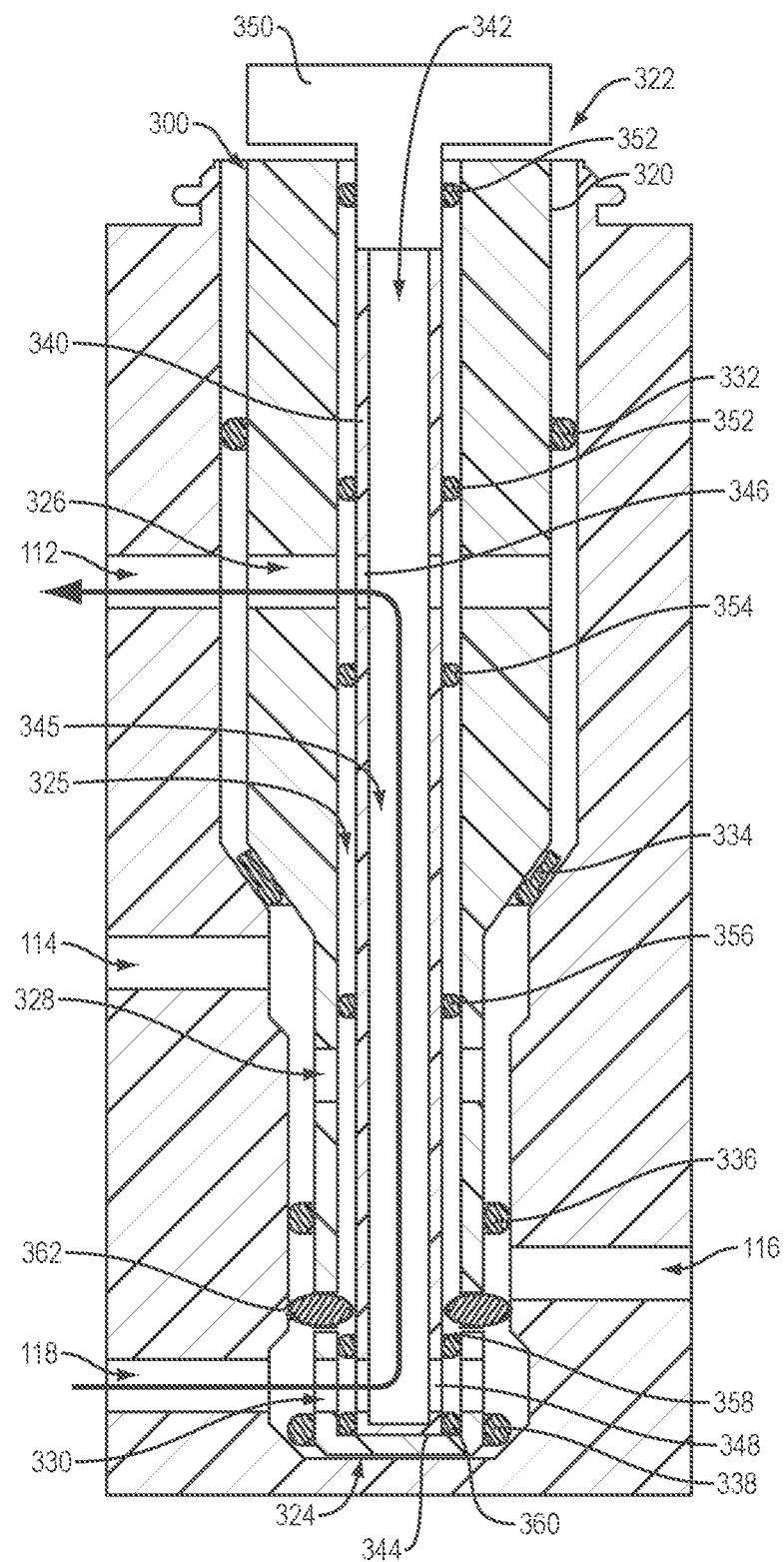

Referring to FIGS. 4A-4C, in one embodiment, an endoscopic system of the present disclosure may include an endoscopic valve 400 (e.g., air/water valve, etc.) with the same (or similar) elements as recited in the endoscopic valve 300 of FIGS. 3A-3C, and further including an expandable member 362 (e.g., seal, etc.) extending through a sidewall of the valve stem 320 and around a full circumference of the valve stem 320 between the second and third ports 328, 330. In various embodiments, the flow of air and/or water through the endoscopic valve 400 when the valve stem 320 and inner member 340 are in the first configuration (FIG. 4A) or second configuration (FIG. 4B) may be identical to the corresponding flow of air and/or water as described above for FIGS. 3A-3C, respectively (see arrows in FIG. 4A flowing from the air inlet port 114 to the open proximal end 342 and from air inlet port 114 to air outlet port 112 and arrow in FIG. 4B flowing from the water inlet port 118 to the water outlet port 1162).

Referring to FIG. 4C, in the third configuration, air may be blocked from flowing proximally through the channel 325 of the valve stem 320, e.g., by the sealing contact between the seventh seal 356 and the inner surface of the channel 325, and may be blocked from flowing distally through the channel 325 of the valve stem 320 and through the second opening 348 of the inner member 340 e.g., by the sealing contact between the eighth seal 358, as discussed above.

In addition, in the third configuration, the inner member 340 may extend through the expandable member 362 (e.g., through an opening/aperture, not shown) to move the expandable member 362 from a first configuration (e.g., the non-expanded configuration of FIGS. 4A-4B) to a second configuration (e.g., the expanded configuration of FIG. 4C). In the first configuration, the expandable member 362 may not form a sealing contact with an inner surface of the housing. By comparison, in the second configuration the expandable member 362 may sealingly contact an inner surface of the housing 110 proximal to the water inlet port 118 and distal to the water outlet port 116 (e.g., between the water inlet and outlet ports 118, 116), to block/prevent the flow of water through the water outlet port 116 of the housing 110 and through the second water channel 132b. In addition, in the second configuration, water may flow from the processing system 120, through the first water channel 132a, through the water inlet port 118 of the housing 110, through the third port 330 of the valve stem 320, through the second opening 348 and lumen 345 of the inner member 340, through the first opening 346 of the inner member 340, through the first port 326 of the valve stem 320, through the air outlet port 112 of the housing 110 and through second air channel 130b (see arrow in FIG. 4C flowing from the water inlet port 118 to the air outlet port 112).

Figure 5A:
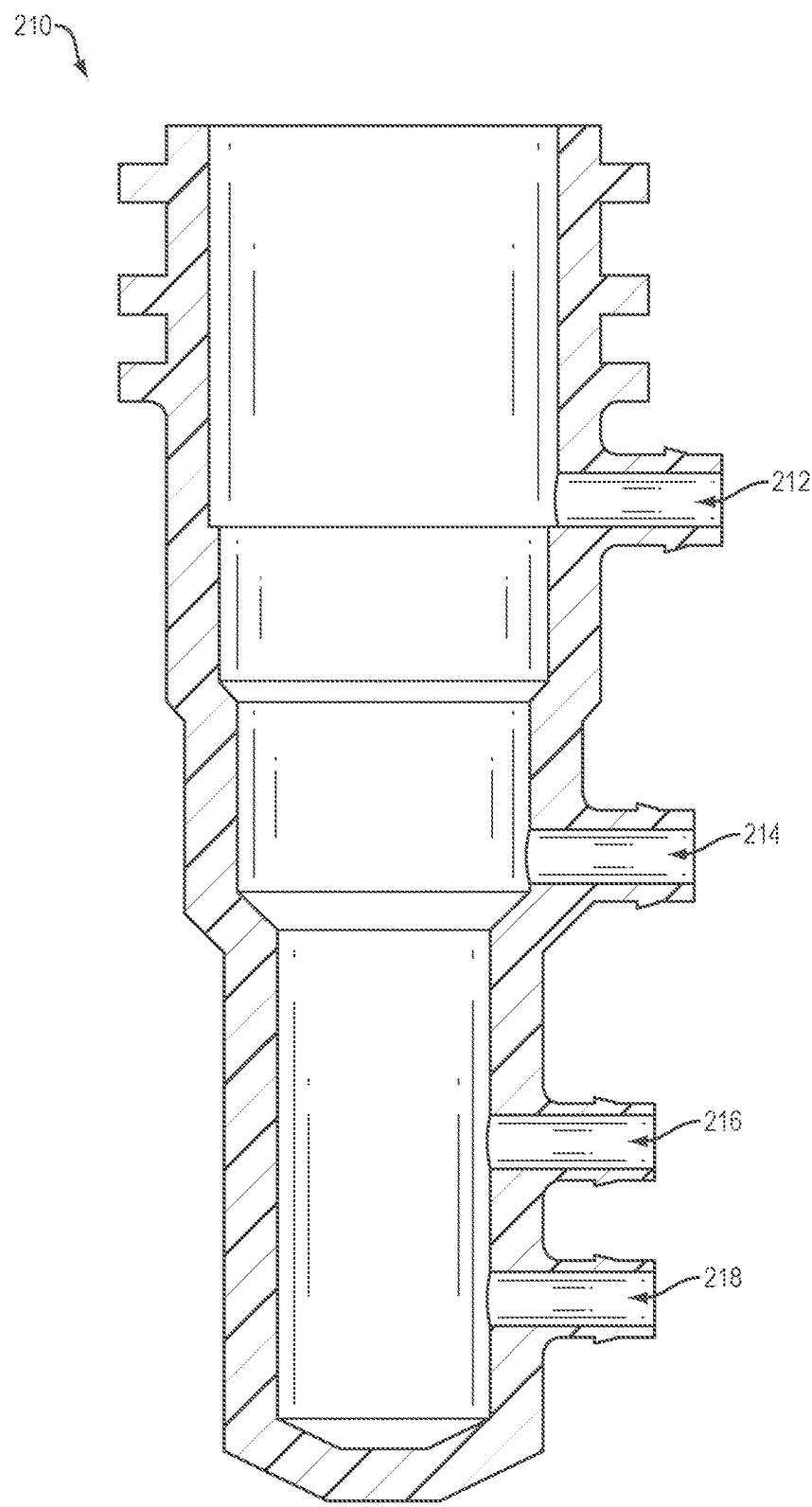
FIGS. 5A-5E provide perspective views of an endoscopic valve, according to one embodiment of the present disclosure.
Figure 5B:
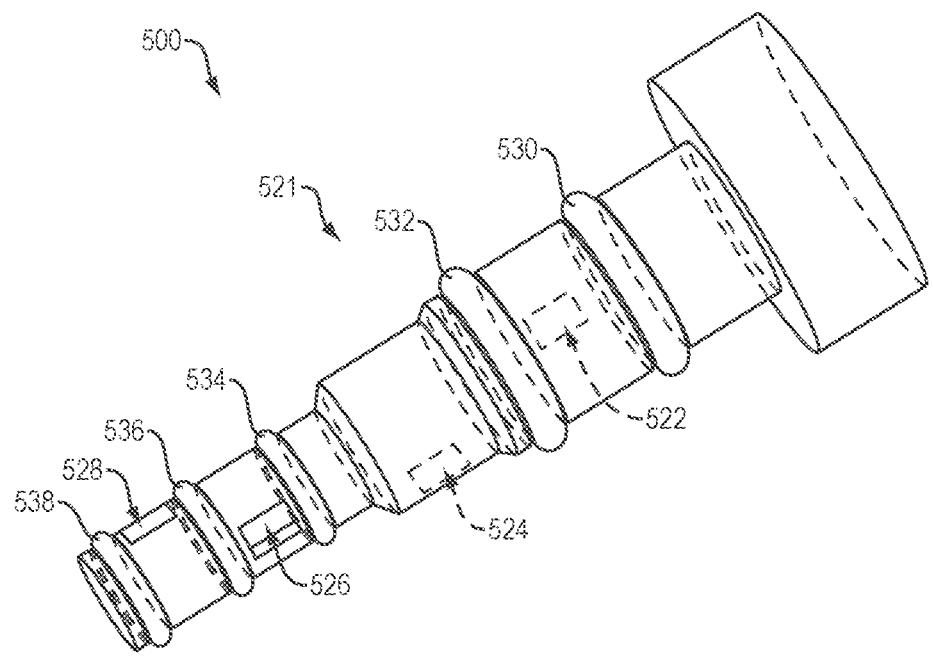
Figure 5C:
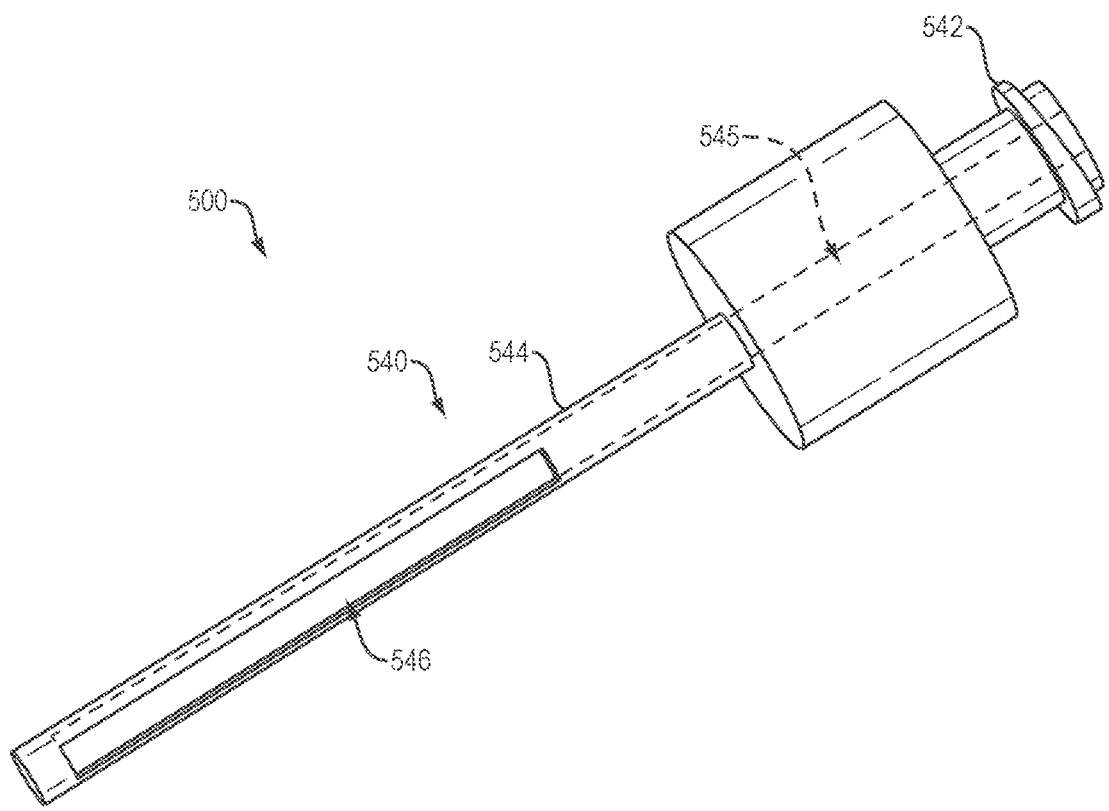

Referring to FIGS. 5A-5C, in one embodiment, an endoscopic system of the present disclosure may include an endoscopic adaptor 500 disposable within a housing 210 (FIG. 5A) of an endoscope handle 100 (FIG. 1A).

Referring to FIG. 5A, in one embodiment, the housing 210 may include an air outlet port 212, an air inlet port 214, a water outlet port 216 and a water inlet port 218 formed within (e.g., extend through) different respective portions/sections of a sidewall of the housing 210. For example, the air outlet port may be proximal to the air inlet port, the air inlet port may be proximal to water outlet port and the water outlet port may be proximal to the water inlet port. In various embodiments, the air and water inlet and outlet ports may be arranged differently, as long as they align appropriately with their corresponding inlet and outlet channels of the endoscope. In various embodiments, the air outlet port 212 may be configured to fluidly receive (e.g., fluidly connected to, in fluid communication with, etc.) a proximal end of the second air channel 130b extending through the insertion tube 128, the air inlet port 214 may be configured to fluidly receive a distal end of the first air channel 130a extending through the length of tubing 126, the water outlet port 216 may be configured to fluidly receive a proximal end of the second water channel 132b extending through the insertion tube 128 and the water inlet port 218 may be configured to fluidly receive a distal end of the first water channel 132a extending through the length of tubing 126.

In one embodiment, an adaptor 500 of the present disclosure may include an outer housing 521 (FIG. 5B) and an inner member 540 (FIG. 5C) rotatably and coaxially disposed within the outer housing 521. In various embodiments, the adaptor 500 may be configured to move (e.g., switch) between a first configuration (e.g., post-operative/post-procedural pre-cleaning configuration), a second configuration (e.g., post-operative/post-procedural pre-cleaning configuration), a third configuration (e.g., post-operative/post-procedural pre-cleaning configuration) and a fourth configuration (e.g., post-operative/post-procedural pre-cleaning configuration) within the housing 210.

Referring to FIG. 5B, in one embodiment, the outer housing 521 may include a longitudinal axis with first 522, second 524, third 526 and fourth 528 openings formed within (e.g., extend through) different radial portions/sections along the longitudinal axis. For example, each opening may be offset along a different 90° radial portion along the longitudinal axis and around a full 360° circumference of the outer housing 521. A first seal 530 may be disposed around an outer surface of the outer housing 521 (e.g., a full circumference of the outer housing) proximal to the first opening 522. A second seal 532 may be disposed around an outer surface of the outer housing 521 (e.g., a full circumference of the outer housing) distal to the first opening 522 and proximal to the second opening 524 (e.g., between the first and second openings). A third seal 534 may be disposed around an outer surface of the outer housing 521 (e.g., a full circumference of the outer housing) distal to the second opening 524 and proximal to the third opening 526 (e.g., between the second and third openings). A fourth seal 536 may be disposed around an outer surface of the outer housing 521 (e.g., a full circumference of the outer housing) distal to the third opening 526 and proximal to the fourth opening 528 (e.g., between the third and fourth openings). A fifth seal 538 may be disposed around an outer surface of the outer housing 521 (e.g., a full circumference of the outer housing) distal to the fourth opening 528.

Referring to FIG. 5C, in one embodiment, the inner member 540 may include a port 542 (e.g., proximal luer port) attached to or integrally formed with a central member 544. A channel 545 may extend through the proximal port 542 and a portion of the central member 544. An elongate window 546 may be formed within (e.g., extend through) a sidewall of the central member and in fluid communication with the channel 545.

Figure 5D:
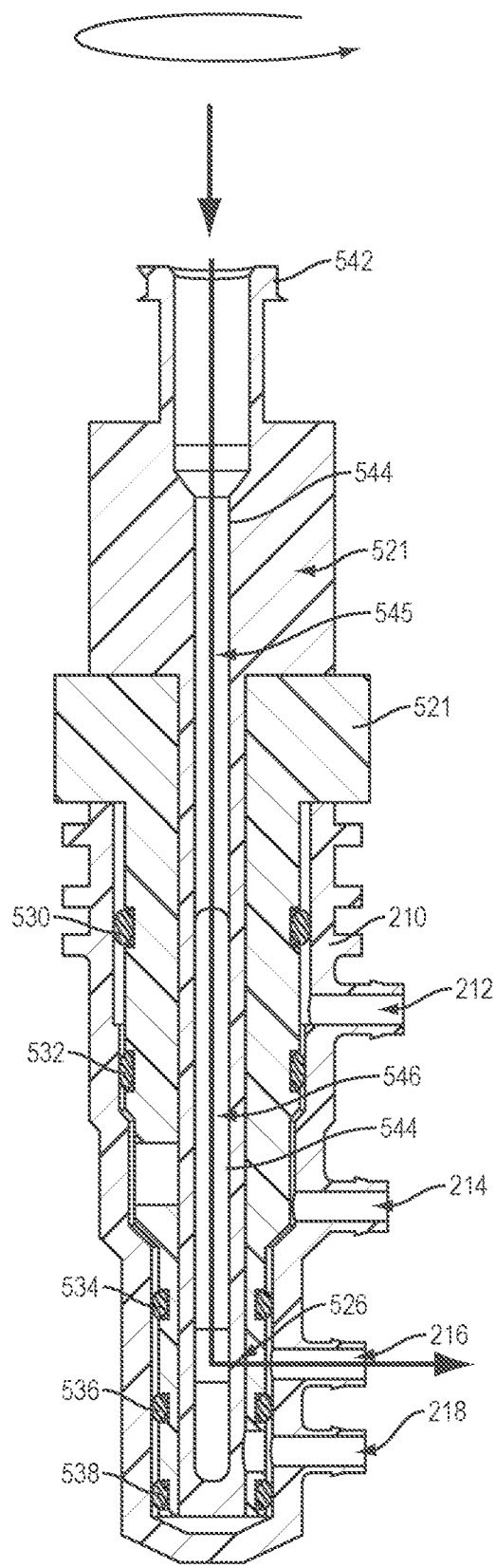
Figure 5E:
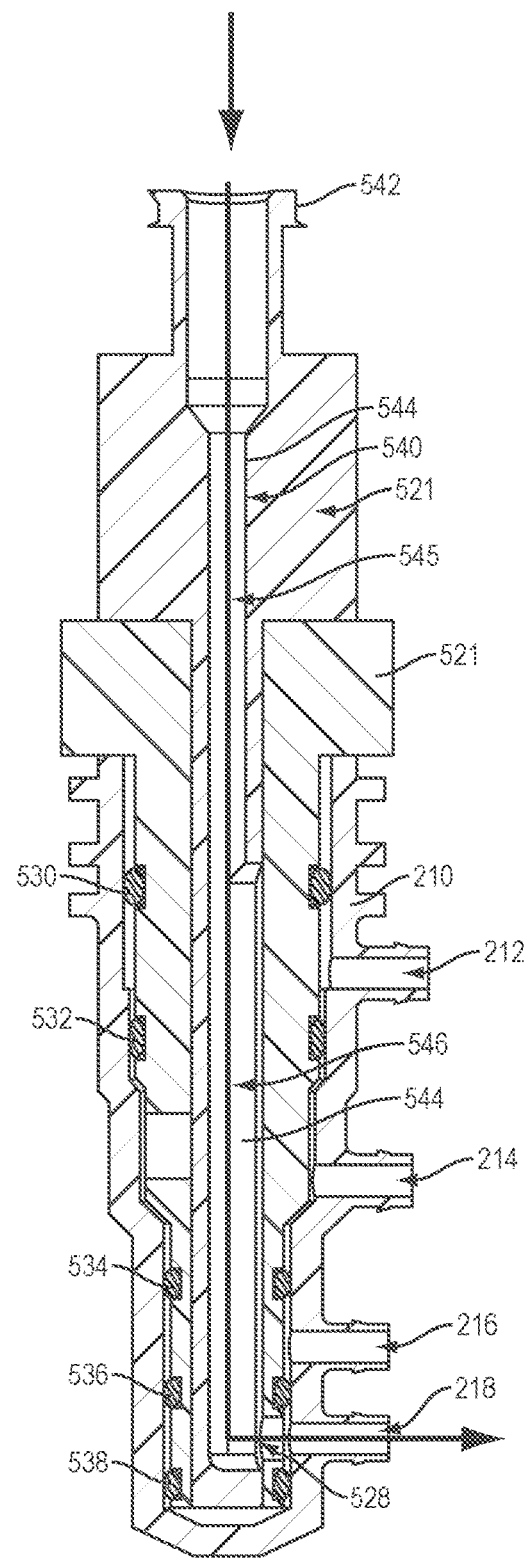

In one embodiment, the outer housing 521 may be configured to receive a portion of the inner member 540 such that the central member 544 may be extendable through the longitudinal axis of the outer housing 521 with the elongate window 546 in fluid communication with each of the first 522, second 524, third 526 and fourth 528 openings (see FIGS. 5D-5E). In various additional embodiments, the first-fifth seals 530-538 may be configured to sealingly contact an inner surface of the housing 210 around (e.g., proximal and distal to) a full circumference of each of the openings 522-528. For example, the first and second seals 530, 532 may be configured to sealingly contact an inner surface of the housing 210 around a full circumference of the first opening 522, the second and third seals 532, 534 may be configured to sealingly contact an inner surface of the housing 210 around a full circumference of the second opening 524, the third and fourth seals 534, 536 may be configured to sealingly contact an inner surface of the housing 210 around a full circumference of the third opening 526, and the fourth and fifth seals 536, 538 may be configured to sealingly contact an inner surface of the housing around a full circumference of the fourth opening 528.

In one embodiment, the inner member 540 may be configured to rotate to four separate/different positions (e.g., first, second, third and fourth configurations) within the outer housing 521 to align the elongate window 546 with a different one of the openings 522, 524, 526, 528, each of which openings are aligned with a different one of the air/water inlet/outlet ports 212, 214, 216, 218 for fluid flow through a selected flow path. For example, in the first configuration, the inner member 540 may be disposed within the outer housing 521 such that the first opening 522 may be substantially aligned with the elongate window 546 and in fluid communication with the air outlet port 212. The second 524, third 526 and fourth 528 openings, e.g., disposed along different 90° radial portions along the longitudinal axis of the outer housing 521, may be out of alignment with the elongate window 546 such that the respective air inlet port 214, water outlet port 216 and water inlet port 218 may be in sealing contact with an inner wall of the outer housing 521. A cleaning solution (e.g., water, enzymatic solution, etc.) or any other fluid may then be introduced from a water source (e.g., syringe, etc.) attached to the proximal port 542 through the channel 545 and elongate window 546 through the air outlet port 212 and the second air channel 130b.

In various embodiments, the inner member 540 may be rotated between any/all of the four separate/different positions to align the elongate window 546 with the desired first, second, third or fourth opening and individually flush (e.g., pre-clean) each of the air/water inlet/outlet ports. For example, from the first configuration, the inner member 540 may be rotated 90° within the outer housing 521 to the second configuration such that the second opening 524 may be substantially aligned with the elongate window 546 and in fluid communication with the air inlet port 214 and the first 522, third 526 and fourth 528 openings may be in sealing contact with an inner wall of the outer housing 521. A cleaning solution may then be introduced from the water source attached to the proximal port 542 through the channel 545, elongate window 546, opening 524, and through the air inlet port 214 and the first air channel 130a.

From the second configuration, the inner member 540 may be rotated 90° within the outer housing 521 to the third configuration (FIG. 5D) such that the third opening 526 may be substantially aligned with the elongate window 546 and in fluid communication with the water outlet port 216 and the first 522, second 524 and fourth 528 openings may be in sealing contact with an inner wall of the outer housing 521. Water may then be introduced from the water source attached to the proximal port 542 through the channel 545, elongate window 546, opening 526 and through the water outlet port 216 and the second water channel 132b.

From the third configuration, the inner member 540 may be rotated 90° within the outer housing 521 to the fourth configuration (FIG. 5E) such that the fourth opening 528 may be substantially aligned with the elongate window 546 and in fluid communication with the water inlet port 218 and the first 522, second 524 and third openings 526 may be in sealing contact with an inner wall of the outer housing 521. Water may then be introduced from the water source attached to the proximal port 542 through the channel 545, elongate window 546, fourth opening 528 and through the water inlet port 218 and the first water channel 132a.

The present disclosure is not limited to an outer housing 521 which includes the first 522, second 524, third 526 and fourth 528 openings disposed along different 90° radial portions along the longitudinal axis. By way of non-limiting example, the first 522, second 524, third 526 and fourth 528 openings may be disposed along a variety of different radial portions (e.g., different 15° radial portion, different 30° radial portions, different 60° radial portions, or combinations/variations thereof).

In various embodiments, the ability to switch between different configurations may allow the respective air/water inlet/outlet ports and/or first/second air/water channels to be individually pre-cleaned for a duration or fluid volume as determined to be appropriate by a medical professional. For example, the air outlet port 112 and second air channel 130b may require a longer pre-cleaning step than the water outlet port 116 and second water channel 132b. In addition, the ability of the adaptor to be fluidly attached to a separate water source may allow the pre-cleaning steps to be performed independently of the processing system, thereby allowing the processing system to be available for additional medical procedures.

Figure 6A:
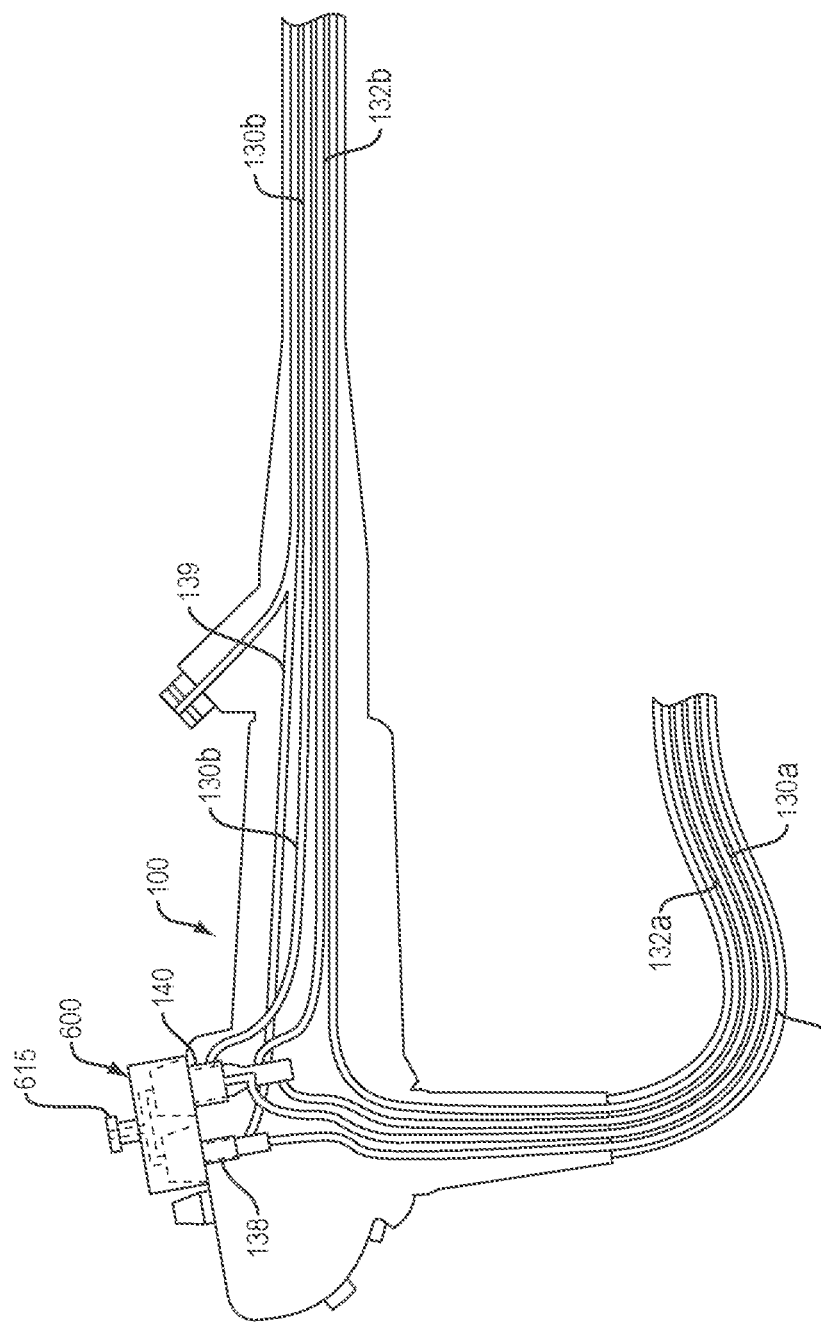
FIGS. 6A-6B provide perspective views of an endoscopic valve, according to one embodiment of the present disclosure.
Figure 6B:
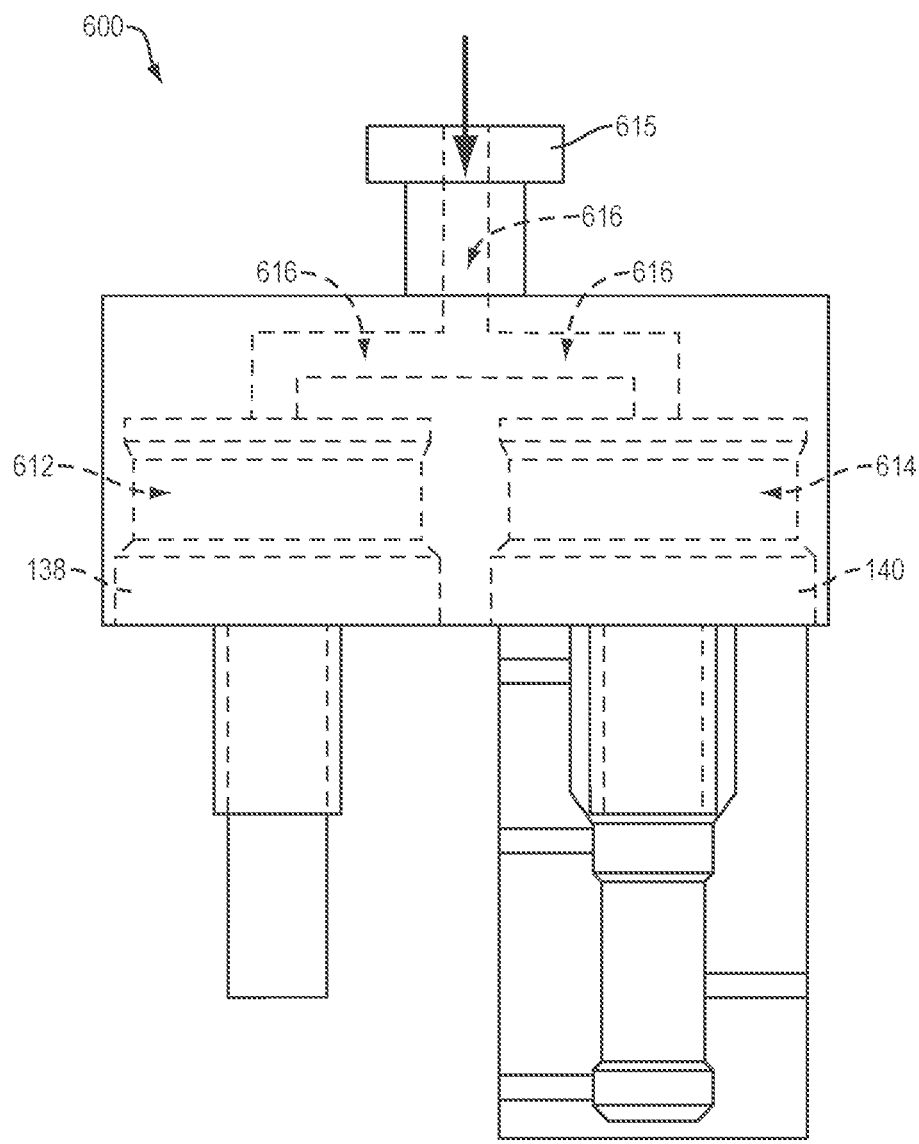

Referring to FIGS. 6A-6B, in one embodiment, an endoscopic system of the present disclosure may include an adaptor 600 configured to fluidly attach to a suction valve 138 and air/water valve 140 of an endoscope handle 100. The adaptor 600 may include first and second recessed portions 612, 614 configured to sealingly receive/engage an outer surface of the suction valve and air/water valve, respectively. A port 615 (e.g., proximal luer port) may be attached to or integrally formed with the adaptor 600. A channel 616 may extend through the port 615 and into first and second recessed portions. The port 615 may be configured to fluidly receive a water source (e.g., syringe, not shown). Water may then be introduced from the water source (e.g., syringe, etc.) through the channel 616 and into the suction valve and air/water valve to simultaneously flush (e.g., pre-clean) the biopsy/suction channel 139 (e.g., fluidly connected to the suction valve) and the first air channel 130a, first water channel 132a, second air channel 130b and second water channel 132b (e.g., fluidly connected to the air/water valve, as discussed above). In various embodiments, the ability of the adaptor 600 to be fluidly attached to a separate water source may allow the pre-cleaning steps to be performed independently of the processing system, thereby allowing the processing system to be available for additional medical procedures.

In various embodiments, the adaptor 600 may include a single recessed portion to deliver water through the suction valve independent of the air/water valve, or through the air/water valve independent of the suction valve.

In various embodiments, any of the endoscopic valves 200, 300, 400 and/or adaptors 500, 600 of the present disclosure may further include a surface coated with a disinfecting agent (e.g., detergent, anti-microbial agent, enzymatic agent, etc.) such that the flow of water through the endoscopic valves and/or adaptors may dissolve the disinfecting agent and carry the disinfecting agent into the various air and water channels described above.

The present disclosure is not limited to the flow of air and water through the disclosed endoscopic valves and endoscopic systems, but may include a variety of biologically compatible and/or inert cleaning solutions, gases and fluids.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An endoscopic valve, comprising:
   a valve stem, comprising:
   a proximal channel with a proximal opening and a distal channel with a distal opening, the proximal and distal channels defining a contiguous channel, a first port formed within a sidewall of the valve stem and in fluid communication with the proximal channel, and
   a second port formed within the sidewall of the valve stem and in fluid communication with the proximal channel;
   a first seal disposed around an outer surface of the valve stem and distal to the first port;
   a second seal disposed around the outer surface of the valve stem and distal to the second port;
   a third seal disposed around the outer surface of the valve stem and distal to the second seal;
   a gating member slidably disposed within the proximal channel, wherein the gating member is configured to move between a first position in sealing contact with the first port and a second position in sealing contact with the second port, and wherein a lumen extends through the gating member; and
   a valve insert disposed between the proximal and distal channels.

2. An endoscopic system, comprising:
   the endoscopic valve of claim 1; and
   a modular attachment insertable into the proximal channel of the valve stem to move the gating member from the first position to the second position and to move the valve insert from a first position to a second position.

3. An endoscopic system, comprising:
   a housing of an endoscope, comprising:
   a housing of an endoscope, the housing comprising:
   an air outlet port formed within a sidewall of the housing,
   an air inlet port formed within the sidewall of the housing and distal to the air outlet port, a water outlet port formed within the sidewall of the housing and distal to the air inlet port, and a water inlet port formed within the sidewall of the housing and distal to the water outlet port; and the endoscopic valve of claim 1, wherein the valve stem is movable between a first configuration and a second configuration within the housing of the endoscope.

4. The endoscopic system of claim 3, wherein in the first configuration, air is flowable from a processing system through the air inlet port and into the valve stem, and in the second configuration, water is flowable from the processing system through the water inlet port, into the valve stem and through the water outlet port.

5. The endoscopic system of claim 4, wherein the air is flowable through a proximal opening of the valve stem into the atmosphere.

6. The endoscopic system of claim 4, wherein the air is flowable through the air outlet port when a proximal opening of the valve stem is blocked.

7. The endoscopic system of claim 3, wherein the valve stem is movable between the first configuration, the second configuration and a third configuration within the housing of the endoscope.

8. The endoscopic system of claim 7, wherein in the first configuration, air is flowable from a processing system through the air inlet port and into the valve stem.

9. The endoscopic system of claim 8, wherein the air is flowable through a proximal opening of the valve stem and into the atmosphere.

10. The endoscopic system of claim 8, wherein the air is flowable through the air outlet port when a proximal opening of the valve stem is blocked.

11. The endoscopic system of claim 7, wherein in the second configuration, water is flowable from a processing system through the water inlet port, into the valve stem and through the water outlet port.

12. The endoscopic system of claim 7, wherein in the third configuration, water is flowable from a processing system through the water inlet port, into the valve stem and through the air outlet port, and water is flowable from the processing system through the water inlet port, into the valve stem and through the water outlet port.

13. An endoscopic system, comprising:
a housing disposable within an endoscope handle;
a length of tubing extending from the endoscope handle to a processing system;
an insertion tube extending from the endoscope handle;
an endoscopic valve movable between a first configuration and a second configuration within the housing, wherein the endoscopic valve comprises a valve stem with a proximal channel and a distal channel;
a gating member slidably disposed within the proximal channel;
a first air channel and a first water channel extending from the processing system to the housing through the length of tubing; and
a second air channel and a second water channel extending from the housing through the insertion tube.

14. The endoscopic system of claim 13, wherein in both the first and second configurations, air is flowable from the processing system through the first air channel and into the valve stem, and
water is flowable from the processing system through the first water channel, into the valve stem and through the second water channel.

15. The endoscopic system of claim 14, wherein the air is flowable through a proximal opening of the endoscopic valve into the atmosphere.

16. The endoscopic system of claim 13, wherein the endoscopic valve is movable between the first configuration, the second configuration and a third configuration within the housing, wherein in the third configuration, water is flowable from the processing system through the first water channel, into the valve stem and through the second air channel, and water is flowable from the processing system through the first water channel, into the valve stem and through the second water channel.

* * * * *